(12) United States Patent
Saint-Remy et al.

(10) Patent No.: US 11,787,849 B2
(45) Date of Patent: Oct. 17, 2023

(54) METHODS AND COMPOUNDS FOR ELIMINATING IMMUNE RESPONSES TO THERAPEUTIC AGENTS

(71) Applicant: IMCYSE SA, Liège (BE)

(72) Inventors: Jean-Marie Saint-Remy, Grez-Doiceau (BE); Luc Vander Elst, Obaix (BE); Vincent Carlier, Enimes (BE)

(73) Assignee: IMCYSE SA, Liège (BE)

( * ) Notice: Subject to any disclaimer, the term of this patent is extended or adjusted under 35 U.S.C. 154(b) by 979 days.

(21) Appl. No.: 15/761,223

(22) PCT Filed: Sep. 23, 2016

(86) PCT No.: PCT/EP2016/072690
§ 371 (c)(1),
(2) Date: Mar. 19, 2018

(87) PCT Pub. No.: WO2017/050966
PCT Pub. Date: Mar. 30, 2017

(65) Prior Publication Data
US 2018/0258154 A1    Sep. 13, 2018

(30) Foreign Application Priority Data
Sep. 25, 2015 (EP) .................................... 15186845

(51) Int. Cl.
| | | |
|---|---|---|
| *A61K 35/12* | (2015.01) | |
| *A61K 8/60* | (2006.01) | |
| *A61K 38/17* | (2006.01) | |
| *A61K 38/18* | (2006.01) | |
| *A61K 38/19* | (2006.01) | |
| *A61K 38/22* | (2006.01) | |
| *A61K 38/36* | (2006.01) | |
| *A61K 39/00* | (2006.01) | |
| *C12N 9/02* | (2006.01) | |
| *C07K 14/74* | (2006.01) | |
| *A61K 39/39* | (2006.01) | |
| *A61K 35/17* | (2015.01) | |
| *A61K 38/00* | (2006.01) | |

(52) U.S. Cl.
CPC ...... *C07K 14/70539* (2013.01); *A61K 39/001* (2013.01); *A61K 39/39* (2013.01); *C12N 9/0004* (2013.01); *A61K 38/00* (2013.01); *A61K 2035/122* (2013.01); *A61K 2039/55505* (2013.01); *A61K 2039/55516* (2013.01); *A61K 2039/572* (2013.01); *A61K 2039/627* (2013.01); *A61K 2039/70* (2013.01); *C07K 2319/40* (2013.01)

(58) Field of Classification Search
None
See application file for complete search history.

(56) References Cited

U.S. PATENT DOCUMENTS

| | | |
|---|---|---|
| 4,599,231 A | 7/1986 | Milich et al. |
| 4,886,782 A | 12/1989 | Good et al. |
| 5,433,948 A | 7/1995 | Thomas et al. |
| 5,552,142 A | 9/1996 | Thomas et al. |
| 5,589,175 A | 12/1996 | Vahlne et al. |
| 5,633,234 A | 5/1997 | August et al. |
| 5,770,202 A | 6/1998 | Thomas et al. |
| 5,773,002 A | 6/1998 | Thomas et al. |
| 5,863,528 A | 1/1999 | Hawley et al. |
| 6,399,383 B1 | 6/2002 | Apt et al. |
| 6,602,509 B1 | 8/2003 | Saint-Remy et al. |
| 6,656,471 B1 | 12/2003 | Sastry et al. |
| 6,759,046 B1 | 7/2004 | Gaudernack et al. |
| 7,157,089 B1 | 1/2007 | Mizzen et al. |
| 7,306,804 B2 | 12/2007 | Sastry et al. |
| 8,999,346 B2 | 4/2015 | Saint-Remy |
| 9,044,507 B2 | 6/2015 | Saint-Remy |
| 9,248,171 B2 | 2/2016 | Saint-Remy |
| 9,249,202 B2 | 2/2016 | Saint-Remy |
| 9,394,517 B2 | 7/2016 | Saint-Remy |
| 9,861,661 B2 | 1/2018 | Saint-Remy |
| 10,023,847 B2 | 7/2018 | Saint-Remy |
| 2003/0049723 A1 | 3/2003 | Zhang et al. |
| 2003/0104570 A1 | 6/2003 | Cabezon Silva et al. |
| 2003/0129205 A1 | 7/2003 | Saint-Remy et al. |
| 2003/0152581 A1 | 8/2003 | Saint-Remy et al. |
| 2004/0077045 A1 | 4/2004 | Zhang et al. |
| 2005/0032039 A1 | 2/2005 | Sastry et al. |
| 2005/0107256 A1 | 5/2005 | Barnwell et al. |
| 2005/0181446 A1* | 8/2005 | Roggen .................. A21D 2/267 435/7.1 |

(Continued)

FOREIGN PATENT DOCUMENTS

| | | |
|---|---|---|
| JP | 2004147649 A | 5/2004 |
| JP | 2010500308 A | 1/2010 |

(Continued)

OTHER PUBLICATIONS

Pipe et al (Haemophilia, 2004, 10 (Suppl. 4): 55-63) (Year: 2004).*

(Continued)

*Primary Examiner* — Michael Szperka
*Assistant Examiner* — Marianne DiBrino
(74) *Attorney, Agent, or Firm* — NIXON & VANDERHYE, PC

(57) ABSTRACT

The invention describes kit of parts of polypeptides comprising: a) a peptide comprising: a1) an MHC class II T cell epitope or a CD1 d-restricted NKT cell epitope, and a2) immediately adjacent to said epitope or separated by at most 7 amino acids from said epitope a [CST]-X(2)-C [SEQ ID NO:7] or C-X(2)-[CST] [SEQ ID NO:8] oxidoreductase motif sequence, and b) a polypeptide comprising: b1) a therapeutic protein and b2) the epitope defined in a1), wherein the epitope sequence is a sequence which differs from the sequence of the protein of b1). The therapeutic protein, in combination with the peptide, is used to prevent an immune response against the therapeutic protein.

12 Claims, No Drawings

Specification includes a Sequence List

(56) References Cited

U.S. PATENT DOCUMENTS

| | | |
|---|---|---|
| 2005/0196386 A1 | 9/2005 | Blazar et al. |
| 2005/0202044 A1 | 9/2005 | Mizzen et al. |
| 2006/0182763 A1 | 8/2006 | Kim et al. |
| 2006/0211091 A1 | 9/2006 | Zhang et al. |
| 2006/0216301 A1 | 9/2006 | Tahara et al. |
| 2006/0269561 A1 | 11/2006 | Paterson et al. |
| 2007/0160620 A1 | 7/2007 | Mizzen et al. |
| 2007/0184023 A1 | 8/2007 | Rasmussen et al. |
| 2008/0176247 A1 | 7/2008 | Chou et al. |
| 2009/0012004 A1 | 1/2009 | Sette et al. |
| 2010/0033088 A1 | 2/2010 | Saint Remy |
| 2010/0068193 A1 | 3/2010 | Brunsvig et al. |
| 2010/0183652 A1 | 7/2010 | Page et al. |
| 2010/0203083 A1 | 8/2010 | Lux et al. |
| 2010/0303866 A1 | 12/2010 | Saint-Remy |
| 2010/0330088 A1 | 12/2010 | Saint-Remy |
| 2011/0002903 A1 | 1/2011 | Saint-Remy |
| 2011/0110964 A1 | 5/2011 | Saint-Remy |
| 2011/0111395 A1 | 5/2011 | Saint-Remy |
| 2011/0111502 A1 | 5/2011 | Saint-Remy |
| 2012/0009678 A1 | 1/2012 | Saint-Remy |
| 2013/0095133 A1 | 4/2013 | Klatzmann et al. |
| 2013/0259885 A1 | 10/2013 | Saint Remy |
| 2014/0370044 A1 | 12/2014 | Saint-Remy |
| 2014/0377299 A1 | 12/2014 | Saint-Remy |
| 2015/0110821 A1 | 4/2015 | Saint-Remy |
| 2015/0216901 A1 | 8/2015 | Saint-Remy |
| 2016/0091492 A1 | 3/2016 | Saint-Remy et al. |
| 2016/0108103 A1 | 4/2016 | Saint-Remy |
| 2016/0194367 A1 | 7/2016 | Saint-Remy |
| 2016/0250255 A1 | 9/2016 | Saint Remy |
| 2016/0339121 A1 | 11/2016 | Saint-Remy |
| 2017/0100466 A1 | 4/2017 | Saint-Remy |
| 2018/0228912 A1 | 8/2018 | Saint-Remy et al. |
| 2018/0258154 A1 | 9/2018 | Saint-Remy |
| 2018/0346887 A1 | 12/2018 | Saint-Remy |
| 2019/0106477 A1 | 4/2019 | Vander Elst |

FOREIGN PATENT DOCUMENTS

| | | |
|---|---|---|
| WO | WO-8504103 A1 | 9/1985 |
| WO | WO-9205800 A1 | 4/1992 |
| WO | WO-9308279 A1 | 4/1993 |
| WO | WO-9405790 A1 | 3/1994 |
| WO | WO-9740852 A1 | 11/1997 |
| WO | WO-9958552 A2 | 11/1999 |
| WO | WO-0029008 A2 | 5/2000 |
| WO | WO-0170263 A1 | 9/2001 |
| WO | WO-0200892 A1 | 1/2002 |
| WO | WO-02095051 A2 | 11/2002 |
| WO | WO-02097070 A1 | 12/2002 |
| WO | WO-03072731 A2 | 9/2003 |
| WO | WO-2004018667 A1 | 3/2004 |
| WO | WO-2004024766 A1 | 3/2004 |
| WO | WO-2005012502 A2 | 2/2005 |
| WO | 2005042575 A2 | 5/2005 |
| WO | WO-2005039613 A1 | 5/2005 |
| WO | WO-2005042575 A2 | 5/2005 |
| WO | WO-2005086781 A2 | 9/2005 |
| WO | WO-2006059529 A1 | 6/2006 |
| WO | WO-2007135684 A2 | 1/2007 |
| WO | WO-2007104715 A2 | 9/2007 |
| WO | 2008017517 A1 | 2/2008 |
| WO | WO-2009042215 A3 | 4/2009 |
| WO | 2009101204 A2 | 8/2009 |
| WO | 2009101205 A2 | 8/2009 |
| WO | 2009101206 A2 | 8/2009 |
| WO | 2009101208 A2 | 8/2009 |
| WO | WO-2009100505 A1 | 8/2009 |
| WO | WO-2009101204 A2 | 8/2009 |
| WO | WO-2009101207 A1 | 8/2009 |
| WO | WO-2009106073 A2 | 9/2009 |
| WO | WO-2010037395 A2 | 4/2010 |
| WO | 2012069568 A2 | 5/2012 |
| WO | 2013121296 A1 | 8/2013 |
| WO | WO-2013113076 A1 | 8/2013 |
| WO | 2015063176 A1 | 5/2015 |
| WO | WO-2015063176 A1 | 5/2015 |
| WO | 2016059236 A2 | 4/2016 |
| WO | WO-2016059236 A1 | 4/2016 |

OTHER PUBLICATIONS

Girardi et al (JBC, 2016, 291 (20): 10677-10683) (Year: 2016).*
Merriam-Webster Dictionary, 2022, pp. 1/12-12/12 (Year: 2022).*
Imcyse Technology Platform (2022, 2 pages) (Year: 2022).*
Miao et al (Human Gene Therapy, 2016, 27(3): 230-243) (Year: 2016).*
Zhang D et al., "Preclinical experimental models of drug metabolism and disposition in drug discovery and development," Acta Pharmaceutica Sinica B 2012;2(6):549-561.
De Groot A et al., "Immunogenicity of protein therapeutics," Trends in Immunology, vol. 28, No. 11, 482-490, 2007.
PCT International Search Report and Written Opinion dated Feb. 15, 2017 for PCT International Patent Application No. PCT/EP2016/072690, 19 pages.
Carlier V A et al., "Increased Synapse Formation Obtained by T Cell Epitopes Containing a CxxC Motif in Flanking Residues Convert CD4+ T Cells into Cytolytic Effectors", Plos One, vol. 7, No. 10, Oct. 9, 2012, p. e45366, 16 pages.
Abrahimians E M et al., "MHC class II-restricted epitopes containing an oxidoreductase activity prompt CD4+ T cells with apoptosis-inducing properties," Frontiers in Immunology, vol. 6, Sep. 2, 2015 (Sep. 2, 2015), pp. 1-5.
Fomenko D E et al., "Identity and functions of CxxC-derived motifs," Biochemistry, vol. 42, No. 38, Sep. 30, 2003 (Sep. 30, 2003), pp. 11214-11225.
PCT International Search Report and Written Opinion dated May 4, 2018 in connection with PCT International Patent Application No. PCT/EP2018/055501.
European Summons to attend oral proceedings pursuant to Rule 115(1) EPC in connection with European Patent Application No. 13709300.1, Dec. 21, 2018.
Davis M M et al., "Interrogating the repertoire: broadening the scope of peptide-MHC multimer analysis," Nature Reviews, Immunology, Aug. 2011, vol. 11, 551-558.
PCT International Search Report and Written Opinion dated Jun. 26, 2017 for PCT International Patent Application No. PCT/EP2017/059302, 11 pages.
Matsuda J L et al., "CD1d-restricted iNKT cells, the 'Swiss-Army Knife' of the immune system," Current Opinion in Immunology, vol. 20, No. 3, Jun. 1, 2008, pp. 358-368.
Database Geneseq (online), Jan. 26, 2017 "Human preproInsulIn (PPI) antigenic peptide, Seq Id 164," XP002770300, retrieved from EBI accession No. GSP:BDK51134.
Abrahimians E M et al., "Thioreductase-Containing Epitopes Inhibit the Development of Type 1 Diabetes in the NOD Model," Frontiers in Immunology, vol. 7, Mar. 2, 2016, XP055371835.
Chapter III Immune Molecules.
Pillai A B et al., "Host NKT Cells Can Prevent Graft-versus-Host Disease and Permit Graft Antitumor Activity after Bone Marrow Transplantation," The Journal of Immunology, 2007, 178: 6242-6251.
Hemmer B et al., "Minimal peptide length requirements for CD4+ T cell clones-implications for molecular mimicry and T cell survival," International Immunology, vol. 12, No. 3, pp. 375-383, 2000.
Vignali D A A et al., "Amino Acid Residues that Flank Core Peptide Epitopes and the Extracellular Domains of CD4 Modulate Differential Signaling through the T Cell Receptor," J. Exp. Med., vol. 179, Jun. 1994, 1945-1956.
Lovitch S B et al., "Amino-Terminal Flanking Residues Determine the Conformation of a Peptide-Class II MBC Complex," J Immunol 2006; 176:2958-2968.
Japanese Final Decision for Rejection in connection with Japanese Patent Application No. 2016-516134.

(56) References Cited

OTHER PUBLICATIONS

Abrahimians et al., "MHC class II-restricted epitopes containing an oxidoreductase activity prompt CD4+ T cells with apoptosis-inducing properties," Frontiers in Immunology, vol. 6, 2 (2015), pp. 1-5.
Aleksza et al., "Altered cytokine expression of peripheral blood lymphocytes in polymyositis and dermatomyositis," (2005) Ann. Rheum. Dis. 64, 1485-1489.
Aley & Gillin, "Giardia lambiia: post-translational processing and status of exposed cysteine residues in TSA 417, a variable surface antigen" (1993) Exp Parasitol. 77, 295-305.
Apostolou et al., "Evidence for two subgroups of CD4-CD8-NKT cells with distinct TCR alpha beta repertoires and differential distribution in lymphoid tissues," J Immunol. 165(5):2481-90 (2000).
Appella et al., "Analysis of the structure of naturally processed peptides bound by class I and class II major histocompatibility complex molecules." EXS. (1995) 73:105-19.
Arunachalam et al., "Enzymatic reduction of disulfide bonds in lysosomes: Characterization of a Gamma-interferon-inducible lysosomal thiol reductase (GILT)," (2000) Proc. Natl. Acad. Sci USA, vol. 97, No. 2, 745-750.
Ascherio et al., "Environmental factors in multipie sclerosis," Expert Rev Neurother. 13(12 S):3-9 (2013).
Azoury-Ziadeh et al., "T-Helper Epitopes Identified Within the E6 Transforming Protein of Cervical Cancer-Associated Human Papillomavirus Type 16," Viral Immunology, 1999, 12(4): 297-312.
Balato et al., "Natural killer T cells: An unconventional T-cell subset with diverse effector and regulatory functions," Journal of Investigative Dermatology 129: 1628-1642 (2009).
Batten et al., "Immune response to stem cells and strategies to induce tolerance," (2007) Phil. Trans. R. Soc. B 362, 1343-1356.
Boisgerault et al., "Differential roles of direct and indirect allorecognition pathways in the rejection of skin and corneal transplants," (2009) Transplantation 87(1): 16-23.
Bolivar et al., "Molecular cloning of a zinc finger autoantigen transiently associated with interphase nucleolus and mitotic centromeres and midbodies. Orthologous proteins with nine CXXC motifs highly conserved form nematodes to humans," J. Biol, Chem., vol. 274, (1999), p. 36456-36464.
Bower et al., "Two Members of the Thioredoxin-h Family Interact with the Kinase Domain of a *Brassica* S Locus Receptor Kinase," (1996) The plant cell, vol. 8, 1641-1650.
Braun et al., "Acute rejection in the absence of cognate recognition of allograft by T cells," J. Immunol., vol. 166, No. 8, (2001), pp. 4879-4883.
Brinks et al., "Immunogenicity of Therapeutic Proteins: The Use of Animal Models," Pharm Res (2011) 28:2379-2385.
Brinster et al., "Bone Marrow-Derived Dendritic Cells Reverse the Anergic State of CD4+CD25+ T Cells without Reversing Their Suppressive Function," (2005), The Journal of Immunology 175:7332-7340.
Brinster et al., "Costimulatory effects of IL-1 on the expansion/differentiation of CD4+CD25+Foxp3+and CD4+CD25+Foxp3—T cells," J. Leukoc. Biol., vol. 84, (2008), pp. 480-487.
Cao et al., "Prevention of gene transfer-induced Inhibitor formation by nasal administration of human F.IX T cell epitope In a murine model of hemophilia B.," Blood, vol. 104(11), (2004), pp. 121A-122A.
Capon et al., "The CD4-gp120 Interaction and Aids Pathogenesis," (1991) Ann. Rev. Immunol 9, 649-678.
Caro-Aguilar et al., "Chimeric epitopes delivered by polymeric synthetic linear peptides induce I protective immunity to malaria," Microbes Infect. 7:1324-1337 (2005).
Carlier et al., "Increased Synapse Formation Obtained by T cell Epitopes Containing a CxxC Motif in Flanking Residues Convert CD4+ T Cells into Cytolytic Effectors," PLOS One, Oct. 2012, vol. 7, Issue 10, e45366, pp. 1-16.
Carlier et al., "Control of asthma by in vitro-induced allergen-specific regulatory T cells in the mouse," Munksgaard Allergy. 62(Suppl 83):555 (Abstract 1 616) (2007).
Castano et al., "Peptide binding and presentation by mouse CD1," Science 269: 223-226 (1995).
Cavone et al., "Long-term suppression of EAE relapses by pharmacological impairment of epitope spreading," Br J Pharmacol 171 (6):1501-9 (2014).
Celis et al., "Induction of anti-tumor cytotoxic T lymphocytes in normal humans using primary cultures and synthetic peptide epitopes," Proc Natl Acad Sci USA. Mar. 15, 1994;91 (6):2105-9.
Chen et al., "Induction of dominant transpianation tolerance by an altered peptide ligand of the male antigen Dby," (2004) J Clin. Invest. 113(12), 1754-1762.
Chen et al., "Glucocorticoid amplifies Il-2-dependent expansion of functional FoxP3+CD4+CD25+ T regulatory cells in vivo and enhances their capacity to suppress EAE," (2006) Eur. J. Immunol. 36, 2139-2149.
Chuanlin ed., Molecular Immunology, Fudan University Press, Shanghai Medical College Press; publication date; May 2001; pp. 428-429, 433-436 (English language translation provided) (15 pages).
Corthay et al., "CD4+ T Cells Cooperate with Macrophages for Specific Elimination of MHC Class II-Negative Cancer Cells," (2007) Adv Exp Med Biol. 590, 195-208.
Cotton et al., "Oxidative inhibition of human soluble catechol-O-methyltransferase," (2004) Biol. Chem. vol. 279: 23710-718.
Credo Reference, (2012).
Crellin et al., "Altered activation of AKT is required for the suppressive function of human CD4+CD25+ T regulatory cells," Blood 1 09(5):2014-2022 (2007).
Crompton et al., "Advances and challenges in malaria vaccine development," The Journal of Clinic Investigation, 2010, vol. 120, pp. 4168-4178.
Davids et al., A new family of giardial cysteine-rich non-VSP protein genes and a novel cyst protein, PLOS. One. vol. 1, (2006), e44.
Davis et al., "Interrogating the repertoire: broadening the scope of peptide-MHC multimer analysis," Nature Rev. Immunology, (2011), 11, 551-558.
De La Cruz et al., "The immunologic significance of variation within malaria circumsporozoite protein sequences," J. Immunol., vol. 142, (1989), pp. 3568-3575.
Desmetz et al., "Proteomics-Based Identification of HSP60 as a Tumor-Associated Antigen in Early Stage Breast Cancer and Ductal Carcinoma in situ," Journal of Proteome Research (2008), 7, 3830-3837.
Dobrzanski, "Expanding roles for CD4T cells and their subpopulations in tumor immunity and therapy," Frontiers in Oncology, Mar. 2013, vol. 3, Article 63, pp. 1-19.
Dobrzynski et al., "Prevention of cytotoxic T lymphocyte responses to factor IX-expressing hepatocytes by gene transfer-induced regulatory T cells," Proc. Natl. Acad. Sci. U.S.A., vol. 103, (2006), pp. 4592-4597.
Eberl et al., "Tissue-specific segregation of CD1d-dependent and CD1d-independent NK T cells," J. Immunol., vol. 162, (1999), pp. 6410-6419.
Facktor et al., "Hypersensitivity to tetanus toxoid," J Allergy Clin Immunol. Jul. 1973;52(1): 1-12.
Fan et al., "Co-immunization of BALB/c mice with recombinant immunogens containing G protein fragment and chimeric CTL epitope of respiratory syncytial virus induces enhanced cellular immunity and high level of antibody response," (2005) Vaccine 23, 4453-4461.
Fomenko et al., "Identity and functions of CxxC-derived motifs," Biochemistry, vol. 42, (2003), pp. 11214-11225.
Francois et al., "The CD4+ T-Cell Response of Melanoma Patients to a MAGE-A3 Peptide Vaccine Involves Potential Regulatory T Cells," Cancer Res. 69(10):4335-4345 (2009).
Frankel et al., "Characterization of diphtheria fusion proteins targeted to the human interieukin-3 receptor," Protein Eng. 13(8):575-81 (2000).
Freeman (Molecular Cell Biology, 4th Edition, Lodish et al., Eds, New York, 2000, section 6.3, "Viruses: Structure, Function, and Uses").

(56) References Cited

OTHER PUBLICATIONS

Ge et al., "An hsp 70 fusion protein vaccine potentiates the immune response against Japanese encephalitis virus," (2007) Arch. Viral 152, 125-135.
Geluk et al., "HLA-DR binding analysis of peptides from islet antigens in IDDM," Diabetes, vol. 47, (1998), pp. 1594-1601.
GenBank AA5961 0.1, 1995, p. 1.
GenBank AAA58655.1, 1994, p. 1.
GenBank FPAA051928, 1997, p. 1.
GenBank M77349.1—Skonier et al., "Human transforming growth factor-beta induced gene product (BIGH3) mRNA, complete cds," Jan. 14, 1995 (3 pages).
GenPept PDB 5GSB_A, 2017, pp. 1-2.
Gentile et al., "Thyroglobulin as an autoantigen: what can we learn about immunopathogenicity from the correlation of antigenic properties with protein structure?," (2004) Immunol 112 13-25.
Girardi et al., "Structure of an alpha-helical peptide and lipopeptide bound to the nonclassical major histocompatibility complex (MHC) class 1 molecule CD1 d," J Biol Chem. 291 (20):1 0677-83 (2016).
Gross et al., "Simple conditioning with monospecific CD4+CD25+ regulatory T cells for bone marrow engraftment and tolerance to multiple gene products," Blood, vol. 108, No. 6, (2006), pp. 1841-1848.
Grossman et al., "Differential expression of granzymes A and B in human cytotoxic lymphocyte subsets and T regulatory cells," Blood, vol. 104, (2004), pp. 2840-2848.
Haque, "Cysteinylation of MHC Class II Ligands: Peptide Endocytosis and Reduction Within APC Influences T Cell Recognition. sup.1," (2001) J. Immunol. 166, 4543-4551.
Harris et al., "Prediction of murine MHC class I epitopes in a major house dust mite allergen and induction of T1-type CD8+ T cell responses," (1997) Int. Immunol., vol. 9, No. 2, 273-280.
Haveman et al., "Induction and capture of CD4+ cytotoxic adenoviral specific T-cells in response to pan-DR binding adenoviral epitopes toward immunotherapy," Blood, vol. 106, (2005), Abstract 3238.
Haveman et al., "Novel pan-DR-binding T cell epitopes of adenovirus induce pro-inflammatory cytokines and chemokines in healthy donors," Int Immunol. 18(11):1521-1529 (2006).
Heemskerk et al., "Adenovirus-Specific CD4.sup.+ T Cell Clones Recognizing Endogenous Antigen Inhibit Viral Replication In Vitro through Cognate Interaction," The Journal of Immunology (2006); 177:8851-8859.
Ho et al., "CD4(-)CD8alphaalpha subset of CD1d-restricted NKT cells controls T cell expansion," J Immunol. 172(12):7350-8 (2004).
Hohn et al., "CD4+ tumor-infiltrating lymphocytes in cervical cancer recognize HLA-DR-restricted peptides provided by human papillomavirus-E7," J. Immunol., vol. 163, (1999), pp. 5715-5722.
Hori et al., "Control of regulatory T cell development by the transcription factor Foxp3," Science, vol. 299, (2003), pp. 1057-1061.
HSU et al., "Assessing computational amino acid—turn propensities with a phage-displayed combinatorial library and directed evolution," Structure, (2006), vol. 14, pp. 1499-1510.
Iqbalsyah et al., "The CXXC motif at the N terminus of an .alpha.-helical peptide," (2006) Protein Sci. 15, 1945-1950.
Ise et al., "Naive CD4+ T cells exhibit distinct expression patterns in cytokines and cell surface molecules on their primary responses to varying doses of antigen," J. Immunol., vol. 168, (2002), pp. 3242-3250.
James et al., "HY peptides modulate transplantation responses to skin allografts," Int Immunol. 14(11):1333-1342 (2002).
Janeway et al., Immunobiology, 3rd edition, Garland Press Inc., 1997, p. G: 11.
Janssens et al., "CD4+ CD25+ T Cells Lyse Antigen-Presenting B Cells by Fas-Fas Ligand Interaction in an Epitope-Specific Manner. sup.1," (2003) J. Immunol. 171, 4604-4612.
Jensen, "Acidification and Disulfide Reduction Can be Sufficient to Allow Intact Proteins to Bind MHC," (1993) J. Immunol. 150, No. 8, 3347-3356.
Joffre et al., "Induction of antigen-specific tolerance to bone marrow allografts with CD4+CD25+ T lymphocytes," Blood, vol. 103, No. 11, (2004), pp. 4216-4221.
Karin et al., "Reversal of Experimental Autoimmune Encephalomyelitis by a Soluble Peptide Variant of a Myelin Basic Protein Epitope: T Cell Receptor Antagonism and Reduction of Interferon $\gamma$ and Tumor Necrosis Factor $\alpha$ Production," J Exp Med. Dec. 1, 1994;180(6):2227-37.
Kasprowicz et al., "Tracking of Peptide-Specific CD4+ T-Cell Responses After and Acute Resolving Viral Infection: a Study of Parovirus 819," Journal of Virology, Nov. 2006, vol. 80, No. 22, pp. 11209-11217.
Khare et al., "HLA class II transgenic mice authenticate restriction of myelin oligodendrocyte glycoprotein-specific immune response implicated in multiple sclerosis pathogenesis," (2003) Int. Immunol. 15, No. 4, 535-546.
Klebanoff et al.,"Therapeutic cancer vaccines: are we there yet?" Immunol. Rev. (2011), 239: 27-44.
Kumar et al., "Twins and endocrinology," Indian J Endocrinol Metab. Nov. 2014;18(Suppl 1):S48-52. doi: 10.4103/2230-8210. 145074.
Lewin et al., "Effects of substitutions in the CXXC active-site motif of the extracytoplasmic hioredoxin ResA," Biochem. J. (2008), 414, 81-91.
Li et al., "Twisting immune responses for allogeneic stem cell therapy," (2009) World J Stem Cells 1(1), 30-35.
Li Pira et al., "High throughput T epitope mapping and vaccine development," The Journal of Biomedicine and Technology, (2010), vol. 2010, 12 pages.
Lindqvist et al., "Both CD4+ FoxP3+ and CD4+ FoxP3- T cells from patients with B-cell malignancy express cytolytic markers and kill autologous leukaemic B cells in vitro," Immunology 133:296-306 (2011).
Louis et al., "Contrasting CD25hiCD4+ T cells/FOXP3 patterns in chronic rejection and operational drug-free tolerance," Transplantation, vol. 81, (2006), pp. 398-407.
Mach et al., "Regulation of MHC Class II Genes: Lessons from a Disease," (1996) Ann. Rev. Immunol. 14, 301-331.
Maeda et al., "CD1d-independent NKT cells in beta 2-microglobulin-deficient mice have hybrid phenotype and function of NK and T cells," J. Immunol., vol. 172, (2004), pp. 6115-6122.
Maekawa et al., "Evidence for a Domain-Swapped CD4 Dimer as the Coreceptor for Binding to Class II MHC," (2006) J. Immunol. 176(11), 6873-6878.
Markovic-Plese et al., "T cell recognition of immunodominant and cryptic proteolipid protein epitopes in humans," J Immunol. 155(2):982-92 (1995) (12 pages).
Marti et al., "Conformationally Correct Expression of Membrane-Anchored Toxoplasma gondii SAG1 in the Primitive Protozoan Giardia duodenalis," Infection and Immunity, vol. 70, No. 2, Feb. 2002, p. 1014-1016.
Massilamany et al., "Detection of autoreactive CD4 T cells using major histocompatibility complex class II dextramers," BMC Immunology, (2011), 12:40.
Matsuda et al., "CD1 d-reslricted iNKT cells, the 'Swiss-Army Knife' of the immune system," Current Opinion in Immunology, vol. 20, No. 3, Jun. 1, 2008, pp. 358-368.
Matthias et al, "Disulfide exchange in domain 2 of CD4 is required for entry of HIV-1," (2002) Nature Immunol 3, No. 8, 727-732.
MedlinePlus Medical Dictionary (Merriam Webster, Inc., 2017).
Merkler et al., "Myelin oligodendrocyte glycoprotein-induced experimental autoimmune encephalomyelitis in the common marmoset reflects the immunopathology of pattern II multiple sclerosis lesions," Multiple Sclerosis 12:369-374 (2006).
Moldovan et al., "CD4 Dimers Constitute the Functional Component Required for T Cell Activation," The Journal of Immunology (2002), 169:6261-6268.
Nepom, "MHC class II tetramers," The Journal of Immunology, (2012), 188, 2477-2482.
Nielsen et al., "Quantitative Predictions of Peptide Binding to Any HLA-DR Molecule of Known Sequence: NetMHCIIpan," PLOS Comp. Biol., 2008 4(7): 4(7): e1000107.

(56) References Cited

OTHER PUBLICATIONS

Ochoa-Garay et al., "The Ability of Peptides to Induce Cytotoxic T Cells In Vivo Does Not Strongly Correlate With Their Affinity for the H-2L$^d$ Molecule: Implications For Vaccine Design and Immunotherapy," Mol Immunol (1997) 34(3):273-81.
Okubo et al., "Analysis of HLA-DRB1 0901-binding HPV-16 E7 helper T cell epitopel," (2004) J Obstet Gynaecol Res. 30(2), 120-129.
Oliviera et al., "Insights into the Specificity of Thioredoxin Reductase—Thioredoxin Interactions. A Structural and Functional Investigation of the Yeast Thioredoxin System," (2010) Biochemistry 49, 3317-3326.
Papanastasiou et al. "Primary structure and biochemical properties of a variant-specific surface protein of Giardia," Molecular and Biochemical Parasitology 86 (1997) 13-27.
Park et al., "Redox Regulation Facilitates Optimal Peptide Selection by MHC Class I during Antigen Processing," Cell, (2006), 127:369-382.
Peterson, "Regulatory T-cells, diverse phenotypes integral to immune homeostasis and suppression," Toxic Path. 40(2):186-204 (2012).
Printout from NetM HCIIpan Server—prediction results dated Sep. 26, 2018, one page.
Qin et al., "Fusion protein of CDR mimetic peptide with Fc inhibit TNF-alpha induced cytotoxicity," Mol. Immunol., vol. 43, (2006), pp. 660-666.
Quintana et al., "Epitope spreading as an early pathogenic event in pediatric multiple sclerosis," Neurology 83(24):2219-26 (2014).
Rammensee et al., "MHC Ligands and Peptide Motifs," 1997, Springer, New York & Austin, Texas, USA, p. 317.
Rancaniello, "How many viruses on earth?" Virology Blog (2013), virology.ws/2013/09/06/how-many-viruses-on-earth/.
Reznik et al., "Indirect Allorecognition of Mismatched Donor HLA Class II Peptides in Lung Transplant Recipients with Bronchiolitis Obliterans Syndrome," 2001, Am. J. Transpl. vol. 1: 228-235.
Roep et al., "The problems and promises of research into human immunology and autoimmune disease," (2012) Nature Med 18(1) 48-53.
Roopenian et al., "The immunogenomics of minor histocompatibility antigens," Immunol. Rev., vol. 190, (2002), pp. 86-94.
Roper et al., "SARS vaccines: where are we?", 2009, Expert Review of Vaccines, vol. 8, pp. 887-898.
Saez-Borderias et al, "Expression and function of NKG2D in CD4+ T cells specific for human cytomegalovirus," Eur. J. Immunol., vol. 36, (2006), pp. 3198-3206.
Santin et al., "Human Papillomavirus Type 16 and 18 E7-Pulsed Dendritic Cell Vaccination of Stage IB or IIA Cervical Cancer Patients: a Phase I Escalating-Dose Trial," (2008) J. Virol. 82, No. 4, 1968-1979.
Savoldo et al., "Generation of EBV-Specific CD4+ Cytotoxic T Cells from Virus Naive Individuals.sup.1,"(2002) J Immunol. 168(2), 909-918.
Schrieber et al., "Tumor immunogenicity and responsiveness to cancer vaccine therapy: The state of the art," Seminar. Immunol. 22:105-112, (2010).
Schultz et al., "A MAGE-A3 Peptide Presented by HLA-DP4 is Recognized on Tumor Cells by CD4+ Cytolytic T Lymphocytes1," Cancer Research 60, 6272-6275, Nov. 16, 2000.
Sette et al., "HLA supertypes and supermotifs: a functional perspective on HLA polymorphism," (1998) Curr Opinion Immunol. 10, 478-482.
Sette et al., "Epitope-based vaccines: an update on epitope identification, vaccine design and delivery," 2003, Current Opinion in Immunology, vol. 15, pp. 461-470.
Shi et al., "A novel plasma membrane-bound thioredoxin from soybean," (1996) Plant Mol. Biol. 32, 653-662 (Abstract).
Stenstrom et al., "Natural killer T-cell populations in C57BL/6 and NK1.1 congenic BALB.NK mice—a novel thymic subset defined by BALB.NK mice," Immunology, vol. 114, (2005), pp. 336-345.

Straub et al., "Allelic variation in GAD1 (GAD67) is associated with schizophrenia and influences cortical function and gene expression," Molecular Psychiatry (2007) 12, 854-869.
Sundar et al., "Generation of Epstein-Bar virus antigen-specific suppressor T cells in vitro," Int. J. Cancer, vol. 35, (1985), pp. 351-357.
Taylor et al., "T regulatory cells and allergy," Microbes and Infection, vol. 7, (2005), pp. 1049-1055.
Texier et al., "On the diversity and heterogeneity of H-2.sup.d-restricted determinants and T cell epitopes from the major bee venom allergen," (1999) Int Immunol. 11, 1313-1325.
Thomson et al., "Targeting a Polyepitope Protein Incorporating Multiple Class II-Restricted Viral Epitopes to the Secretory/Endocytic Pathway Facilitates Immune Recognition by CD4+ Cytotoxic T Lymphocytes: a Novel Approach to Vaccine Design," J. of Virol, 1998, 72(3):2246-2252.
Tindle et al., "A "public" T-helper epitope of the E7 transforming protein of human papillomavirus 16 provides cognate help for several E7 B-cell epitopes from cervical cancer-associated human papillomavirus genotypes," (1991) Proc Natl. Acad. Sci 88, 5887-5891.
Tisch et al., "Antigen-specific immunotherapy: Is it a real possibility to combat T-cell-mediated autoimmunity?" PNAS 91: 437-438, (1994).
Toyokawa et al., "Relative Contribution of Direct and Indirect Allorecognition in Developing Tolerance After Liver Transplantation," 2008 Liver Transpl. 14(3) 346-357.
Tsuji et al., "Antigen-specific, CD4+CD25+ regulatory T cell clones induced in Peyer's patches," Int. Immunol., vol. 15, (2003),pp. 525-534.
UniProt P01906.2, 2017, p. 1-6.
UniProt O15523.2, 2017, pp. 1-7.
Voo et al., "Functional characterization of EBV-encoded nuclear antigen 1-specific CD4+ helper and regulatory T cells elicited by in vitro peptide stimulation," Cancer Res., vol. 65, (2005), pp. 1577-1586.
Wang et al., "Generation and characterization of HLA-A*2.1 restricted and Prostein 31-39 specific NKT cell lines," Acta Academiae Medicine Militaris Tertiae. 28(16):1652-1655 (2006) (English language translation provided) (11 pages).
Wang, "Immune suppression by tumor-specific CD4+ regulatory T-cells in cancer," Semin. Cancer Biol., vol. 16, (2006), pp. 73-79.
Weissert et al., "MHC Class II-Regulated Central Nervous System Autoaggression and T Cell Responses in Peripheral Lymphoid Tissues Are Dissociated in Myelin Oligodendrocyte Glycoprotein-Induced Experimental Autoimmune Encephalomyelitis.sup.1," (2001) J. Immunol. 166, 7588-7599.
Wekerle et al., "Autoimmunity's next top models," (2012) Nature Med. 18(1), 66-70.
Wiker et al., "Cloning, expression and significance of MPT53 for identification of secreted proteins of *Mycobacterium tuberculosis*," Microb. Pathog., vol. 26, (1999), pp. 207-219.
Wobus et al., "Embryonic Stem Cells: Prospects for Developmental Biology and Cell Therapy," (2005) Physiol Rev 85: 635-678.
Wood et al., "Regulatory T cells in Transplantation tolerance," Nat. Rev. Immunol., vol. 3, (2003), pp. 199-210.
Wooldridge et al., "Tricks with tetramers: how to get the most from multimeric peptide-MHC," Immunology, 2009, 126(2):147-64.
Written Description Training Materials, Revision 1, Mar. 25, 2008, U.S. Patent and Trademark Office.
Wu et al., "Engineering an intracellular pathway for major histocompatibility complex class II presentation of antigens," (1995) Proc. Natl. Acad. Sci. 92, 11671-11675.
Zeng at al., "Crystal structure of mouse CD1: An MHC-like fold with a large hydrophobic binding groove," Science 277: 339-345 (1997).
Zhang et al., "A MAGE-3 Peptide Presented by HLA-DR1 to CD4+ T Cells That Were Isolated from a Melanoma Patient Vaccinated with a MAGE-3 Protein," J Immunol. 171:219-225 (2003).
Zhao et al., "Activated CD4+CD25+ T cells selectively kill B Lymphocytes," Blood, vol. 107, No. 10; pp. 3925-3932; May 15, 2006.

(56) References Cited

OTHER PUBLICATIONS

Final Office Action dated Jan. 20, 2012 issued in U.S. Appl. No. 12/377,048, filed Feb. 10, 2009, related application.
Final Office Action dated Aug. 9, 2012 issued in U.S. Appl. No. 12/377,048, filed Feb. 10, 2009, related application.
Non-Final Office Action dated Apr. 20, 2015 issued in U.S. Appl. No. 12/377,048, filed Feb. 10, 2009, related application.
Notice of Allowance dated Sep. 22, 2015 issued in U.S. Appl. No. 12/377,048, filed Feb. 10, 2009, related application.
Non-Final Office Action dated Feb. 20, 2018 issued in U.S. Appl. No. 14/976,259, filed Dec. 21, 2015, related application.
Final Office Action dated Oct. 26, 2018 issued in U.S. Appl. No. 14/976,259, filed Dec. 21, 2015, related application.
Advisory Action dated Feb. 4, 2019 issued in U.S. Appl. No. 14/976,259, filed Dec. 21, 2015, related application.
Non-Final Office Action dated May 17, 2019 issued in U.S. Appl. No. 14/976,259, filed Dec. 21, 2015, related application.
Non-Final Office Action dated May 20, 2014 issued in U.S. Appl. No. 12/735,744, filed Aug. 13, 2010, related application.
Final Office Action dated Jun. 5, 2015 issued in U.S. Appl. No. 12/735,744, filed Aug. 13, 2010, related application.
Notice of Allowance dated Sep. 28, 2015 issued in U.S. Appl. No. 12/735,744, filed Aug. 13, 2010, related application.
Non-Final Office Action dated Jan. 9, 2014 issued in U.S. Appl. No. 12/735,744, filed Aug. 13, 2010, related application.
Non-Final Office Action dated Nov. 25, 2014 issued in U.S. Appl. No. 12/735,744, filed Aug. 13, 2010, related application.
Non-Final Office Action dated Dec. 1, 2017 issued in U.S. Appl. No. 14/980,832, filed Dec. 28, 2015 related application.
Non-Final Office Action dated Sep. 11, 2018 issued in U.S. Appl. No. 14/980,832, filed Dec. 28, 2015 related application.
Final Office Action dated Jan. 8, 2019 issued in U.S. Appl. No. 14/980,832, filed Dec. 28, 2015 related application.
Notice of Allowance dated Apr. 3, 2019 issued in U.S. Appl. No. 14/980,832, filed Dec. 28, 2015 related application.
Non-Final Office Action dated Jul. 11, 2013 issued in U.S. Appl. No. 12/735,739, filed Aug. 13, 2010 related application.
Final Office Action dated Feb. 20, 2014 issued in U.S. Appl. No. 12/735,739, filed Aug. 13, 2010 related application.
Non-Final Office Action dated Jan. 11, 2016 issued in U.S. Appl. No. 12/735,739, filed Aug. 13, 2010 related application.
Final Office Action dated Aug. 31, 2016 issued in U.S. Appl. No. 12/735,739, filed Aug. 13, 2010 related application.
Non-Final Office Action dated Oct. 2, 2018 issued in U.S. Appl. No. 15/388,398, filed Dec. 22, 2016 related application.
Final Office Action dated Apr. 15, 2019 issued in U.S. Appl. No. 15/388,398, filed Dec. 22, 2016 related application.
Non-Final Office Action dated Jan. 22, 2013 issued in U.S. Appl. No. 12/735,740, filed Aug. 13, 2010 related application.
Final Office Action dated Jul. 10, 2013 issued in U.S. Appl. No. 12/735,740, filed Aug. 13, 2010 related application.
Non-Final Office Action dated Apr. 1, 2014 issued in U.S. Appl. No. 12/735,740, filed Aug. 13, 2010 related application.
Notice of Allowance dated Oct. 2, 2014 issued in U.S. Appl. No. 12/735,740, filed Aug. 13, 2010 related application.
Notice of Allowability dated Mar. 3, 2015 issued in U.S. Appl. No. 12/735,740, filed Aug. 13, 2010 related application.
Advisory Action dated Mar. 20, 2017 issued in U.S. Appl. No. 14/589,134, filed Jan. 5, 2015 related application.
Final Office Action dated Jan. 19, 2018 issued in U.S. Appl. No. 14/589,134, filed Jan. 5, 2015 related application.
Final Office Action dated Dec. 2, 2016 issued in U.S. Appl. No. 14/589,134, filed Jan. 5, 2015 related application.
Notice of Allowance dated Feb. 21, 2019 issued in U.S. Appl. No. 14/589,134, filed Jan. 5, 2015 related application.
Non-Final Office Action dated Jul. 14, 2017 issued in U.S. Appl. No. 14/589,134, filed Jan. 5, 2015 related application.
Non-Final Office Action dated Aug. 17, 2016 issued in U.S. Appl. No. 14/589,134, filed Jan. 5, 2015 related application.
Non-Final Office Action dated Oct. 5, 2018 issued in U.S. Appl. No. 14/589,134, filed Jan. 5, 2015 related application.
Non-Final Office Action dated Jan. 18, 2013 issued in U.S. Appl. No. 12/735,742, filed Aug. 13, 2010 related application.
Non-Final Office Action dated Aug. 24, 2017 issued in U.S. Appl. No. 14/450,722, filed Aug. 4, 2014 related application.
Final Office Action dated Dec. 28, 2017 issued in U.S. Appl. No. 14/450,722, filed Aug. 4, 2014 related application.
Advisory Action dated May 9, 2018 issued in U.S. Appl. No. 14/450,722, filed Aug. 4, 2014 related application.
Non-Final Office Action dated Jan. 14, 2019 issued in U.S. Appl. No. 14/450,722, filed Aug. 4, 2014 related application.
Non-Final Office Action dated Jun. 17, 2016 issued in U.S. Appl. No. 13/988,925, filed Jun. 6, 2013 related application.
Final Office Action dated Dec. 28, 2016 issued in U.S. Appl. No. 13/988,925, filed Jun. 6, 2013 related application.
Non-Final Office Action dated Nov. 9, 2017 issued in U.S. Appl. No. 13/988,925, filed Jun. 6, 2013 related application.
Notice of Allowance dated Mar. 26, 2018 issued in U.S. Appl. No. 13/988,925, filed Jun. 6, 2013 related application.
Non-Final Office Action dated Feb. 23, 2017 issued in U.S. Appl. No. 14/375,324, filed Jul. 29, 2014 related application.
Final Office Action dated Oct. 30, 2017 issued in U.S. Appl. No. 14/375,324, filed Jul. 29, 2014 related application.
Non-Final Office Action dated Jun. 25, 2018 issued in U.S. Appl. No. 14/375,324, filed Jul. 29, 2014 related application.
Final Office Action dated Mar. 25, 2019 issued in U.S. Appl. No. 14/375,324, filed Jul. 29, 2014 related application.
Non-Final Office Action dated Sep. 7, 2018 issued in U.S. Appl. No. 14/894,221, filed Nov. 25, 2015 related application.
Notice of Allowance dated Apr. 15, 2019 issued in U.S. Appl. No. 14/894,221, filed Nov. 25, 2015 related application.
Non-Final Office Action dated Sep. 18, 2018 issued in U.S. Appl. No. 15/516,045, filed Mar. 31, 2017 related application.
Final Office Action dated Feb. 13, 2019 issued in U.S. Appl. No. 15/516,045, filed Mar. 31, 2017 related application.
Non-Final Office Action dated Jun. 8, 2018 issued in U.S. Appl. No. 15/151,868, filed May 11, 2016 related application.
Final Office Action dated Mar. 19, 2019 issued in U.S. Appl. No. 15/151,868, filed May 11, 2016 related application.

\* cited by examiner

SEQUENCE LISTING

<160> NUMBER OF SEQ ID NOS: 40

<210> SEQ ID NO 1
<211> LENGTH: 7
<212> TYPE: PRT
<213> ORGANISM: Artificial Sequence
<220> FEATURE:
<223> OTHER INFORMATION: Cd1d binding petide motif
<220> FEATURE:
<221> NAME/KEY: VARIANT
<222> LOCATION: (1)..(1)
<223> OTHER INFORMATION: Xaa is  Phe, Trp, Tyr, His or Thr
<220> FEATURE:
<221> NAME/KEY: VARIANT
<222> LOCATION: (2)..(3)
<223> OTHER INFORMATION: Xaa can be any amino acid
<220> FEATURE:
<221> NAME/KEY: VARIANT
<222> LOCATION: (4)..(4)
<223> OTHER INFORMATION: Xaa is Val, Ile, Leu or Met
<220> FEATURE:
<221> NAME/KEY: VARIANT
<222> LOCATION: (5)..(6)
<223> OTHER INFORMATION: Xaa can be any amino acid

```
<220> FEATURE:
<221> NAME/KEY: VARIANT
<222> LOCATION: (7)..(7)
<223> OTHER INFORMATION: Xaa is Phe, Trp, Tyr, His or Thr

<400> SEQUENCE: 1

Xaa Xaa Xaa Xaa Xaa Xaa Xaa
1               5

<210> SEQ ID NO 2
<211> LENGTH: 4
<212> TYPE: PRT
<213> ORGANISM: Artificial Sequence
<220> FEATURE:
<223> OTHER INFORMATION: C-X(2)-C redox motif
<220> FEATURE:
<221> NAME/KEY: VARIANT
<222> LOCATION: (2)..(3)
<223> OTHER INFORMATION: Xaa can be any amino acid

<400> SEQUENCE: 2

Cys Xaa Xaa Cys
1

<210> SEQ ID NO 3
<211> LENGTH: 4
<212> TYPE: PRT
<213> ORGANISM: Artificial Sequence
<220> FEATURE:
<223> OTHER INFORMATION: C-X(2)-S redox motif
<220> FEATURE:
<221> NAME/KEY: VARIANT
<222> LOCATION: (2)..(3)
<223> OTHER INFORMATION: Xaa can be any amino acid

<400> SEQUENCE: 3

Cys Xaa Xaa Ser
1

<210> SEQ ID NO 4
<211> LENGTH: 4
<212> TYPE: PRT
<213> ORGANISM: Artificial Sequence
<220> FEATURE:
<223> OTHER INFORMATION: C-X(2)-T redox motif
<220> FEATURE:
<221> NAME/KEY: VARIANT
<222> LOCATION: (2)..(3)
<223> OTHER INFORMATION: Xaa can be any amino acid

<400> SEQUENCE: 4

Cys Xaa Xaa Thr
1

<210> SEQ ID NO 5
<211> LENGTH: 4
<212> TYPE: PRT
<213> ORGANISM: Artificial Sequence
<220> FEATURE:
<223> OTHER INFORMATION: S-X(2)-C redox motif
<220> FEATURE:
<221> NAME/KEY: VARIANT
<222> LOCATION: (2)..(3)
<223> OTHER INFORMATION: Xaa can be any amino acid

<400> SEQUENCE: 5

Ser Xaa Xaa Cys
1
```

```
<210> SEQ ID NO 6
<211> LENGTH: 4
<212> TYPE: PRT
<213> ORGANISM: Artificial Sequence
<220> FEATURE:
<223> OTHER INFORMATION: T-X(2)-C redox motif
<220> FEATURE:
<221> NAME/KEY: VARIANT
<222> LOCATION: (2)..(3)
<223> OTHER INFORMATION: Xaa can be any amino acid

<400> SEQUENCE: 6

Thr Xaa Xaa Cys
1

<210> SEQ ID NO 7
<211> LENGTH: 4
<212> TYPE: PRT
<213> ORGANISM: Artificial Sequence
<220> FEATURE:
<223> OTHER INFORMATION: [CST]-X(2)-C redox motif
<220> FEATURE:
<221> NAME/KEY: VARIANT
<222> LOCATION: (1)..(1)
<223> OTHER INFORMATION: Xaa is Cys, Ser or Thr
<220> FEATURE:
<221> NAME/KEY: VARIANT
<222> LOCATION: (2)..(3)
<223> OTHER INFORMATION: Xaa can be any amino acid

<400> SEQUENCE: 7

Xaa Xaa Xaa Cys
1

<210> SEQ ID NO 8
<211> LENGTH: 4
<212> TYPE: PRT
<213> ORGANISM: Artificial Sequence
<220> FEATURE:
<223> OTHER INFORMATION: C-X(2)-[CST] redox motif
<220> FEATURE:
<221> NAME/KEY: VARIANT
<222> LOCATION: (2)..(3)
<223> OTHER INFORMATION: Xaa can be any amino acid
<220> FEATURE:
<221> NAME/KEY: VARIANT
<222> LOCATION: (4)..(4)
<223> OTHER INFORMATION: Xaa is Cys, Ser or Thr

<400> SEQUENCE: 8

Cys Xaa Xaa Xaa
1

<210> SEQ ID NO 9
<211> LENGTH: 13
<212> TYPE: PRT
<213> ORGANISM: Artificial Sequence
<220> FEATURE:
<223> OTHER INFORMATION: CLIP peptide

<400> SEQUENCE: 9

Lys Met Arg Met Ala Thr Pro Leu Leu Met Gln Ala Leu
1               5                   10

<210> SEQ ID NO 10
<211> LENGTH: 9
<212> TYPE: PRT
<213> ORGANISM: Artificial Sequence
<220> FEATURE:
<223> OTHER INFORMATION: modified clip
```

```
-continued

<220> FEATURE:
<221> NAME/KEY: VARIANT
<222> LOCATION: (1)..(1)
<223> OTHER INFORMATION: Xaa is Val, Ile, Leu, Met, Phe, Trp, Tyr or His
<220> FEATURE:
<221> NAME/KEY: VARIANT
<222> LOCATION: (2)..(2)
<223> OTHER INFORMATION: Xaa is Arg, Val, Ile, Leu, Met, Phe, Trp, Tyr
      or His
<220> FEATURE:
<221> NAME/KEY: VARIANT
<222> LOCATION: (6)..(6)
<223> OTHER INFORMATION: Xaa is Pro or Arg

<400> SEQUENCE: 10

Xaa Xaa Met Ala Thr Xaa Leu Leu Met
1               5

<210> SEQ ID NO 11
<211> LENGTH: 15
<212> TYPE: PRT
<213> ORGANISM: Artificial Sequence
<220> FEATURE:
<223> OTHER INFORMATION: Padre peptide
<220> FEATURE:
<221> NAME/KEY: MOD_RES
<222> LOCATION: (1)..(1)
<223> OTHER INFORMATION: D_alanine
<220> FEATURE:
<221> NAME/KEY: MOD_RES
<222> LOCATION: (3)..(3)
<223> OTHER INFORMATION: I-cyclohexylalanine
<220> FEATURE:
<221> NAME/KEY: MOD_RES
<222> LOCATION: (13)..(13)
<223> OTHER INFORMATION: D_alanine
<220> FEATURE:
<221> NAME/KEY: MOD_RES
<222> LOCATION: (14)..(14)
<223> OTHER INFORMATION: alpha aminocaproic acid

<400> SEQUENCE: 11

Ala Lys Ala Val Ala Ala Trp Thr Leu Lys Ala Ala Ala Lys Cys
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: hepatitis C fragment 1247-1261

<400> SEQUENCE: 12

Gln Gly Tyr Lys Val Leu Val Leu Asn Pro Ser Val Ala Ala Thr
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: hepatitis C fragment 1535-1550

<400> SEQUENCE: 13

Thr Thr Val Arg Leu Arg Ala Tyr Met Asn Thr Pro Gly Leu Pro Val
1               5                   10                  15

<210> SEQ ID NO 14
<211> LENGTH: 16
<212> TYPE: PRT
<213> ORGANISM: Artificial Sequence
```

```
<220> FEATURE:
<223> OTHER INFORMATION: CxxC redox motif + hepatitis C epitope

<400> SEQUENCE: 14

Cys Pro Tyr Cys Val Arg Val Leu Val Leu Asn Pro Ser Val Ala Ala
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: CxxC redox motif + hepatitis C epitope

<400> SEQUENCE: 15

Cys Pro Tyr Cys Val Arg Tyr Met Asn Thr Pro Gly Leu Pro Val
1               5                   10                  15

<210> SEQ ID NO 16
<211> LENGTH: 482
<212> TYPE: PRT
<213> ORGANISM: Artificial Sequence
<220> FEATURE:
<223> OTHER INFORMATION: fusion protein of hepatitis c fragment and anti
      -CD20 antibody

<400> SEQUENCE: 16

Gln Gly Tyr Lys Val Leu Val Leu Asn Pro Ser Val Ala Ala Thr Thr
1               5                   10                  15

Thr Val Arg Leu Arg Ala Tyr Met Asn Thr Pro Gly Leu Pro Val Gln
            20                  25                  30

Val Gln Leu Gln Gln Pro Gly Ala Glu Leu Val Lys Pro Gly Ala Ser
        35                  40                  45

Val Lys Met Ser Cys Lys Ala Ser Gly Tyr Thr Phe Thr Ser Tyr Asn
    50                  55                  60

Met His Trp Val Lys Gln Thr Pro Gly Arg Gly Leu Glu Trp Ile Gly
65                  70                  75                  80

Ala Ile Tyr Pro Gly Asn Gly Asp Thr Ser Tyr Asn Gln Lys Phe Lys
                85                  90                  95

Gly Lys Ala Thr Leu Thr Ala Asp Lys Ser Ser Ser Thr Ala Tyr Met
            100                 105                 110

Gln Leu Ser Ser Leu Thr Ser Glu Asp Ser Ala Val Tyr Tyr Cys Ala
        115                 120                 125

Arg Ser Thr Tyr Tyr Gly Gly Asp Trp Tyr Phe Asn Val Trp Gly Ala
    130                 135                 140

Gly Thr Thr Val Thr Val Ser Ala Ala Ser Thr Lys Gly Pro Ser Val
145                 150                 155                 160

Phe Pro Leu Ala Pro Ser Ser Lys Ser Thr Ser Gly Gly Thr Ala Ala
                165                 170                 175

Leu Gly Cys Leu Val Lys Asp Tyr Phe Pro Glu Pro Val Thr Val Ser
            180                 185                 190

Trp Asn Ser Gly Ala Leu Thr Ser Gly Val His Thr Phe Pro Ala Val
        195                 200                 205

Leu Gln Ser Ser Gly Leu Tyr Ser Leu Ser Ser Val Val Thr Val Pro
    210                 215                 220

Ser Ser Ser Leu Gly Thr Gln Thr Tyr Ile Cys Asn Val Asn His Lys
225                 230                 235                 240

Pro Ser Asn Thr Lys Val Asp Lys Lys Val Glu Pro Lys Ser Cys Asp
                245                 250                 255
```

```
Lys Thr His Thr Cys Pro Pro Cys Pro Ala Pro Glu Leu Leu Gly Gly
                260                 265                 270

Pro Ser Val Phe Leu Phe Pro Pro Lys Pro Lys Asp Thr Leu Met Ile
            275                 280                 285

Ser Arg Thr Pro Glu Val Thr Cys Val Val Val Asp Val Ser His Glu
        290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
370                 375                 380

Thr Leu Pro Pro Ser Arg Asp Glu Leu Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
450                 455                 460

Glu Ala Leu His Asn His Tyr Thr Gln Lys Ser Leu Ser Leu Ser Pro
465                 470                 475                 480

Gly Lys

<210> SEQ ID NO 17
<211> LENGTH: 13
<212> TYPE: PRT
<213> ORGANISM: Artificial Sequence
<220> FEATURE:
<223> OTHER INFORMATION: modified clip peptide

<400> SEQUENCE: 17

Lys Phe Phe Met Ala Thr Arg Leu Leu Met Gln Ala Leu
1               5                   10

<210> SEQ ID NO 18
<211> LENGTH: 18
<212> TYPE: PRT
<213> ORGANISM: Artificial Sequence
<220> FEATURE:
<223> OTHER INFORMATION: CxxC redox motif + modified clip peptide

<400> SEQUENCE: 18

Cys Pro Tyr Cys Val Arg Phe Phe Met Ala Thr Arg Leu Leu Met Gln
1               5                   10                  15

Ala Leu

<210> SEQ ID NO 19
<211> LENGTH: 181
<212> TYPE: PRT
<213> ORGANISM: Artificial Sequence
<220> FEATURE:
<223> OTHER INFORMATION: EPO + modified clip peptide
```

```
<400> SEQUENCE: 19

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65              70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg Gly Lys Phe Phe Met Ala Thr Arg Leu
                165                 170                 175

Leu Met Gln Ala Leu
            180

<210> SEQ ID NO 20
<211> LENGTH: 14
<212> TYPE: PRT
<213> ORGANISM: Artificial Sequence
<220> FEATURE:
<223> OTHER INFORMATION: apolipoprotein B-100 peptide sequence

<400> SEQUENCE: 20

Leu Phe Leu Lys Ser Asp Gly Arg Val Lys Tyr Thr Leu Asn
1               5                   10

<210> SEQ ID NO 21
<211> LENGTH: 18
<212> TYPE: PRT
<213> ORGANISM: Artificial Sequence
<220> FEATURE:
<223> OTHER INFORMATION: CxxC + redox motif apolipoprotein B-100
      epitope

<400> SEQUENCE: 21

Cys Pro Tyr Cys Leu Phe Leu Lys Ser Asp Gly Arg Val Lys Tyr Thr
1               5                   10                  15

Leu Asn

<210> SEQ ID NO 22
<211> LENGTH: 18
<212> TYPE: PRT
<213> ORGANISM: Artificial Sequence
<220> FEATURE:
<223> OTHER INFORMATION: citrulinnated version of SEQ IDN O 21
<220> FEATURE:
<221> NAME/KEY: MOD_RES
<222> LOCATION: (12)..(12)
<223> OTHER INFORMATION: citrulinne
```

```
<400> SEQUENCE: 22

Cys Pro Tyr Cys Leu Phe Leu Lys Ser Asp Gly Arg Val Lys Tyr Thr
1               5                   10                  15

Leu Asn

<210> SEQ ID NO 23
<211> LENGTH: 411
<212> TYPE: PRT
<213> ORGANISM: Artificial Sequence
<220> FEATURE:
<223> OTHER INFORMATION: apolipoprotein B-100 epitope + alpha
      galactosidase

<400> SEQUENCE: 23

Leu Phe Leu Lys Ser Asp Gly Arg Val Lys Tyr Thr Leu Asn Asp Asn
1               5                   10                  15

Gly Leu Ala Arg Thr Pro Thr Met Gly Trp Leu His Trp Glu Arg Phe
                20                  25                  30

Met Cys Asn Leu Asp Cys Gln Glu Glu Pro Asp Ser Cys Ile Ser Glu
            35                  40                  45

Lys Leu Phe Met Glu Met Ala Glu Leu Met Val Ser Glu Gly Trp Lys
50                  55                  60

Asp Ala Gly Tyr Glu Tyr Leu Cys Ile Asp Asp Cys Trp Met Ala Pro
65                  70                  75                  80

Gln Arg Asp Ser Glu Gly Arg Leu Gln Ala Asp Pro Gln Arg Phe Pro
                85                  90                  95

His Gly Ile Arg Gln Leu Ala Asn Tyr Val His Ser Lys Gly Leu Lys
            100                 105                 110

Leu Gly Ile Tyr Ala Asp Val Gly Asn Lys Thr Cys Ala Gly Phe Pro
        115                 120                 125

Gly Ser Phe Gly Tyr Tyr Asp Ile Asp Ala Gln Thr Phe Ala Asp Trp
    130                 135                 140

Gly Val Asp Leu Leu Lys Phe Asp Gly Cys Tyr Cys Asp Ser Leu Glu
145                 150                 155                 160

Asn Leu Ala Asp Gly Tyr Lys His Met Ser Leu Ala Leu Asn Arg Thr
                165                 170                 175

Gly Arg Ser Ile Val Tyr Ser Cys Glu Trp Pro Leu Tyr Met Trp Pro
            180                 185                 190

Phe Gln Lys Pro Asn Tyr Thr Glu Ile Arg Gln Tyr Cys Asn His Trp
        195                 200                 205

Arg Asn Phe Ala Asp Ile Asp Asp Ser Trp Lys Ser Ile Lys Ser Ile
    210                 215                 220

Leu Asp Trp Thr Ser Phe Asn Gln Glu Arg Ile Val Asp Val Ala Gly
225                 230                 235                 240

Pro Gly Gly Trp Asn Asp Pro Asp Met Leu Val Ile Gly Asn Phe Gly
                245                 250                 255

Leu Ser Trp Asn Gln Gln Val Thr Gln Met Ala Leu Trp Ala Ile Met
            260                 265                 270

Ala Ala Pro Leu Phe Met Ser Asn Asp Leu Arg His Ile Ser Pro Gln
        275                 280                 285

Ala Lys Ala Leu Leu Gln Asp Lys Asp Val Ile Ala Ile Asn Gln Asp
    290                 295                 300

Pro Leu Gly Lys Gln Gly Tyr Gln Leu Arg Gln Gly Asp Asn Phe Glu
305                 310                 315                 320
```

```
Val Trp Glu Arg Pro Leu Ser Gly Leu Ala Trp Ala Val Ala Met Ile
            325                 330                 335

Asn Arg Gln Glu Ile Gly Gly Pro Arg Ser Tyr Thr Ile Ala Val Ala
        340                 345                 350

Ser Leu Gly Lys Gly Val Ala Cys Asn Pro Ala Cys Phe Ile Thr Gln
        355                 360                 365

Leu Leu Pro Val Lys Arg Lys Leu Gly Phe Tyr Glu Trp Thr Ser Arg
    370                 375                 380

Leu Arg Ser His Ile Asn Pro Thr Gly Thr Val Leu Leu Gln Leu Glu
385                 390                 395                 400

Asn Thr Met Gln Met Ser Leu Lys Asp Leu Leu
                405                 410

<210> SEQ ID NO 24
<211> LENGTH: 13
<212> TYPE: PRT
<213> ORGANISM: Artificial Sequence
<220> FEATURE:
<223> OTHER INFORMATION: mycobacterium cell entry protein

<400> SEQUENCE: 24

Asp Pro Ile Glu Leu Asn Ala Thr Leu Ser Ala Val Ala
1               5                   10

<210> SEQ ID NO 25
<211> LENGTH: 17
<212> TYPE: PRT
<213> ORGANISM: Artificial Sequence
<220> FEATURE:
<223> OTHER INFORMATION: redox motif + mycobacterium cell entry protein
      epitope

<400> SEQUENCE: 25

Cys Pro Tyr Cys Asp Pro Ile Glu Leu Asn Ala Thr Leu Ser Ala Val
1               5                   10                  15

Ala

<210> SEQ ID NO 26
<211> LENGTH: 466
<212> TYPE: PRT
<213> ORGANISM: Artificial Sequence
<220> FEATURE:
<223> OTHER INFORMATION: mycobacterium cell entry protein + anti-CD52
      specific antibody

<400> SEQUENCE: 26

Asp Pro Ile Glu Leu Asn Ala Thr Leu Ser Ala Val Ala Gly Gly Gln
1               5                   10                  15

Val Gln Leu Gln Glu Ser Gly Pro Gly Leu Val Arg Pro Ser Gln Thr
            20                  25                  30

Leu Ser Leu Thr Cys Thr Val Ser Gly Phe Thr Phe Thr Asp Phe Tyr
        35                  40                  45

Met Asn Trp Val Arg Gln Pro Pro Gly Arg Gly Leu Glu Trp Ile Gly
    50                  55                  60

Phe Ile Arg Asp Lys Ala Lys Gly Tyr Thr Thr Glu Tyr Asn Pro Ser
65                  70                  75                  80

Val Lys Gly Arg Val Thr Met Leu Val Asp Thr Ser Lys Asn Gln Phe
                85                  90                  95

Ser Leu Arg Leu Ser Ser Val Thr Ala Ala Asp Thr Ala Val Tyr Tyr
            100                 105                 110
```

Cys Ala Arg Glu Gly His Thr Ala Ala Pro Phe Asp Tyr Trp Gly Gln
            115                 120                 125

Gly Ser Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
450                 455                 460

Gly Lys
465

<210> SEQ ID NO 27
<211> LENGTH: 7
<212> TYPE: PRT
<213> ORGANISM: Artificial Sequence
<220> FEATURE:
<223> OTHER INFORMATION: CD1d binding peptide

```
<220> FEATURE:
<221> NAME/KEY: VARIANT
<222> LOCATION: (1)..(1)
<223> OTHER INFORMATION: Xaa can be Phe, Trp, Tyr or His
<220> FEATURE:
<221> NAME/KEY: VARIANT
<222> LOCATION: (2)..(3)
<223> OTHER INFORMATION: Xaa can be any amino acid
<220> FEATURE:
<221> NAME/KEY: VARIANT
<222> LOCATION: (4)..(4)
<223> OTHER INFORMATION: Xaa can be Val, Ile, Leu or Met
<220> FEATURE:
<221> NAME/KEY: VARIANT
<222> LOCATION: (5)..(6)
<223> OTHER INFORMATION: Xaa can be any amino acid
<220> FEATURE:
<221> NAME/KEY: VARIANT
<222> LOCATION: (7)..(7)
<223> OTHER INFORMATION: Xaa can be Phe, Trp, Tyr or His

<400> SEQUENCE: 27

Xaa Xaa Xaa Xaa Xaa Xaa Xaa
1               5

<210> SEQ ID NO 28
<211> LENGTH: 7
<212> TYPE: PRT
<213> ORGANISM: Artificial Sequence
<220> FEATURE:
<223> OTHER INFORMATION: CD1d binding peptide
<220> FEATURE:
<221> NAME/KEY: VARIANT
<222> LOCATION: (1)..(1)
<223> OTHER INFORMATION: Xaa is Phe, Trp or Tyr
<220> FEATURE:
<221> NAME/KEY: VARIANT
<222> LOCATION: (2)..(3)
<223> OTHER INFORMATION: Xaa can be any amino acid
<220> FEATURE:
<221> NAME/KEY: VARIANT
<222> LOCATION: (4)..(4)
<223> OTHER INFORMATION: Xaa is Val, Ile, Leu or Met
<220> FEATURE:
<221> NAME/KEY: VARIANT
<222> LOCATION: (5)..(6)
<223> OTHER INFORMATION: Xaa can be any amino acid
<220> FEATURE:
<221> NAME/KEY: VARIANT
<222> LOCATION: (7)..(7)
<223> OTHER INFORMATION: Xaa is Phe, Trp or Tyr

<400> SEQUENCE: 28

Xaa Xaa Xaa Xaa Xaa Xaa Xaa
1               5

<210> SEQ ID NO 29
<211> LENGTH: 9
<212> TYPE: PRT
<213> ORGANISM: Artificial Sequence
<220> FEATURE:
<223> OTHER INFORMATION: modified clip peptide
<220> FEATURE:
<221> NAME/KEY: VARIANT
<222> LOCATION: (1)..(2)
<223> OTHER INFORMATION: Xaa is Val, Ile, Leu, Met, Tyr, His, Phe or Trp
<220> FEATURE:
<221> NAME/KEY: VARIANT
<222> LOCATION: (6)..(6)
<223> OTHER INFORMATION: Xaa is Arg or Pro

<400> SEQUENCE: 29

Xaa Xaa Met Ala Thr Xaa Leu Leu Met
1               5
```

```
<210> SEQ ID NO 30
<211> LENGTH: 9
<212> TYPE: PRT
<213> ORGANISM: Artificial Sequence
<220> FEATURE:
<223> OTHER INFORMATION: modified clip peptide

<400> SEQUENCE: 30

Phe Phe Met Ala Thr Arg Leu Leu Met
1               5

<210> SEQ ID NO 31
<211> LENGTH: 9
<212> TYPE: PRT
<213> ORGANISM: Artificial Sequence
<220> FEATURE:
<223> OTHER INFORMATION: modified clip peptide

<400> SEQUENCE: 31

Trp Trp Met Ala Thr Arg Leu Leu Met
1               5

<210> SEQ ID NO 32
<211> LENGTH: 9
<212> TYPE: PRT
<213> ORGANISM: Artificial Sequence
<220> FEATURE:
<223> OTHER INFORMATION: modified clip peptide

<400> SEQUENCE: 32

Trp Phe Met Ala Thr Arg Leu Leu Met
1               5

<210> SEQ ID NO 33
<211> LENGTH: 9
<212> TYPE: PRT
<213> ORGANISM: Artificial Sequence
<220> FEATURE:
<223> OTHER INFORMATION: modified clip peptide

<400> SEQUENCE: 33

Phe Trp Met Ala Thr Arg Leu Leu Met
1               5

<210> SEQ ID NO 34
<211> LENGTH: 9
<212> TYPE: PRT
<213> ORGANISM: Artificial Sequence
<220> FEATURE:
<223> OTHER INFORMATION: modified clip peptide

<400> SEQUENCE: 34

Phe Phe Met Ala Thr Pro Leu Leu Met
1               5

<210> SEQ ID NO 35
<211> LENGTH: 9
<212> TYPE: PRT
<213> ORGANISM: Artificial Sequence
<220> FEATURE:
<223> OTHER INFORMATION: modified clip peptide

<400> SEQUENCE: 35

Trp Trp Met Ala Thr Pro Leu Leu Met
1               5
```

```
<210> SEQ ID NO 36
<211> LENGTH: 9
<212> TYPE: PRT
<213> ORGANISM: Artificial Sequence
<220> FEATURE:
<223> OTHER INFORMATION: modified clip peptide

<400> SEQUENCE: 36

Trp Phe Met Ala Thr Pro Leu Leu Met
1               5

<210> SEQ ID NO 37
<211> LENGTH: 9
<212> TYPE: PRT
<213> ORGANISM: Artificial Sequence
<220> FEATURE:
<223> OTHER INFORMATION: modified clip peptide

<400> SEQUENCE: 37

Phe Trp Met Ala Thr Pro Leu Leu Met
1               5

<210> SEQ ID NO 38
<211> LENGTH: 70
<212> TYPE: DNA
<213> ORGANISM: Artificial Sequence
<220> FEATURE:
<223> OTHER INFORMATION: fragment of DNA vector for cloning fusion
      proteins with promiscuous epitope

<400> SEQUENCE: 38
gcacggctcg agggcggaaa gttttcatg gccaccagac tgctgatgca ggcgctgagc      60
tagctagttc                                                            70

<210> SEQ ID NO 39
<211> LENGTH: 16
<212> TYPE: PRT
<213> ORGANISM: Artificial Sequence
<220> FEATURE:
<223> OTHER INFORMATION: promiscuous MHC class II T cell epitope

<400> SEQUENCE: 39

Gly Gly Lys Phe Phe Met Ala Thr Arg Leu Leu Met Gln Ala Leu Ser
1               5                   10                  15

<210> SEQ ID NO 40
<211> LENGTH: 211
<212> TYPE: PRT
<213> ORGANISM: Artificial Sequence
<220> FEATURE:
<223> OTHER INFORMATION: fusion protein of erythropoeitein and
      promiscuous MHC Class II epitope

<400> SEQUENCE: 40

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80
```

```
Met Glu Val Gly Gln Gln Ala Val Glu Val Trp Gln Gly Leu Ala Leu
             85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Arg Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg Val Glu Gly Gly Lys Phe Phe Met Ala Thr Arg Leu Leu Met Gln
            195                 200                 205

Ala Leu Ser
210
```

METHODS AND COMPOUNDS FOR ELIMINATING IMMUNE RESPONSES TO THERAPEUTIC AGENTS

CROSS-REFERENCE TO RELATED APPLICATIONS

This application is a U.S. national stage entry under 35 U.S.C. § 371 of PCT International Patent Application No. PCT/EP2016/072690, filed Sep. 23, 2016, which claims priority to European Patent Application No. 15186845.2, filed Sep. 25, 2015, the contents of which are incorporated herein by reference in their entirety.

FIELD OF THE INVENTION

The present invention relates to modified proteins for use in replacement therapies, gene therapy and gene vaccinations.

The present invention further relates to compounds and methods to prevent an immune response against proteins used in replacement therapies, gene therapy and gene vaccinations.

BACKGROUND OF THE INVENTION

Proteins which are used as therapeutic agents often elicit an immune response which precludes further use. Examples are Factor VIII in the treatment of haemophilia A patients, and antibodies specific for cytokines (e.g. anti-TNF-alpha antibodies) or specific for cell surface markers (e.g. anti-CD20 antibodies). On average 30% of the patients treated by such reagents develop antibodies at concentrations detectable in peripheral blood. In addition, a significant proportion of patients require administration of higher than expected doses of the therapeutic agents, suggesting that antibodies at concentrations below detection neutralise the activity of the agent and/or increase its clearance from the circulation. In all these situations, it would be advantageous to prevent these immune responses.

Gene therapy and gene vaccination rely on viral vectors used to carry out transgenesis. However, viral proteins expressed by these vectors elicit immune responses, reducing the efficiency of transgenesis and preventing re-administration of the transgene. Avoiding such response would allow long-term expression of the transgene, and would reduce the number of viral particles needed to achieve functional transgenesis or vaccination efficiency.

Patent application WO2008017517 describes peptides with a class II-restricted T cell epitope of an antigen and a redox motif sequence and their use in the therapy of a number of diseases. Further details are published in Carlier et al. (2012), *PloS ONE* 7, e45366. The use of such peptides results in the generation of CD4+ T cells with cytolytic properties which induce apoptosis of antigen-presenting cells (presenting the antigen used in the design of the peptide) after cognate interaction with peptide-MHC class II complexes.

Further patent applications of the same inventor disclose the use of this technology to avoid an immune response against therapeutic proteins or antibodies (WO2009101206) or against proteins encoded by the backbone of a viral vector for gene therapy of vaccination (WO2009101204).

Promiscuous MHC class II T cell epitopes binding to a plurality of MHC class II molecules have been described for a variety of antigens.

A fusion protein of VEGF and a promiscuous T helper cell epitope is disclosed in US2007184023.

A fusion protein of zona pellucida protein and a tetanus toxin promiscuous T cell epitope generates antibodies which bind to endogenous zona pellucida protein and act as an anticonceptive (Lou et al. (1995) *J. Immunol.* 155, 2715-2720).

SUMMARY OF THE INVENTION

The present invention provides solutions for the following problems.

In the prior art methods, described above, the sequence of the epitope which is used in the peptide is defined by the sequence of the antigen.

When isolated and fused to the redox motif sequence, such epitope peptide can be subject to proteolytic cleavage, may be difficult to solubilise, or may tend to form internal cystine bridges with the redox motif.

Further, the use of different peptides for different therapeutic proteins makes it difficult to design standard procedures wherein peptides can be administrated at a same concentration and in a same vaccination scheme regardless of the type of therapeutic protein which is used.

The large polymorphism of MHC class II determinants in humans makes it difficult to use a single or a small number of epitopes from one protein to match this polymorphism.

Only for those antigens that contain a promiscuous epitope, or for those antigens wherein different epitopes of an antigen can be identified to circumvent the polymorphism, it is possible to treat any individual independent of his/her HLA type.

If present in a protein, the use of a CD1d-restricted NKT cell peptide epitope can bypass the HLA polymorphism, however not all antigenic proteins contain such peptide sequence.

The present invention allows uncoupling the connection between an antigen containing a T cell epitope and the use of the same epitope to make a peptide with an epitope and a redox motif sequence.

The present invention allows using T cell epitopes which bind to different MHC class II proteins and alleles.

As can be easily understood from the medical uses as described in the present application, and described in more detail below these medical uses require a first administration of the peptide comprising the epitope and the oxidoreductase motif to elicit a population of cytolytic CD4+ against Antigen Presenting Cells (APC) presenting the epitope. This is followed by a second administration of a therapeutic protein or a vector for gene therapy with the newly introduced epitope. Herein the therapeutic protein (or the viral vector protein encoded by the vector) contains the same epitope as present in the peptide used in the first administration. An eventual immune response to the e.g. a therapeutic protein would start with the presentation of epitopes of the therapeutic protein by APC. The APC will not only present the epitopes present in the therapeutic protein itself but also the epitope which has been introduced. As a consequence the APC will be killed by the above cytolytic cells, preventing the clearance of the antigen.

The medical uses of the present invention are based on the separate administration of the two types of polypeptides. They are accordingly referred to by one of the synonyms "combination", "set" or "kit of parts".

An aspect of the invention relates to kits of parts of polypeptides comprising:

a) a peptide comprising:

a1) an MHC class II T cell epitope or a CD1d-restricted NKT cell epitope, and a2) immediately adjacent to said epitope or separated by at most 7 amino acids from said epitope a [CST]-X(2)-C [SEQ ID NO:7] or C-X(2)-[CST] [SEQ ID NO:8]oxidoreductase motif sequence, and b) a polypeptide comprising:
b1) a therapeutic protein and
b2) the epitope defined in a1), wherein the epitope sequence is a sequence which differs from the sequence of the protein of b1).

An aspect of the invention relates to kits of parts of comprising:
a) a peptide comprising:
a1) an MHC class II T cell epitope or a CD1d-restricted NKT cell epitope, and
a2) immediately adjacent to said epitope or separated by at most 7 amino acids from said epitope a [CST]-X(2)-C [SEQ ID NO:7] or C-X(2)-[CST] [SEQ ID NO:8]oxidoreductase motif sequence,
and
b) an expression vector comprising a polynucleotide sequence encoding a polypeptide comprising:
b1) a therapeutic protein and b2) the epitope defined in a1), wherein the epitope sequence is a sequence which differs from the sequence of the protein of b1).

An aspect of the invention relates to kits of parts of comprising:
a) a peptide comprising:
a1) an MHC class II T cell epitope or a CD1d-restricted NKT cell epitope, and
a2) immediately adjacent to said epitope or separated by at most 7 amino acids from said epitope a [CST]-X(2)-C [SEQ ID NO:7] or C-X(2)-[CST] [SEQ ID NO:8]oxidoreductase motif sequence,
and
b) a viral vector for gene therapy or gene vaccination comprising in the backbone a polynucleotide sequence encoding a protein comprising:
b1) a viral vector protein for the function and maintenance of the vector,
b2) the epitope defined in a1), wherein the epitope sequence is a sequence which differs from the sequence of the protein of b1).

Thus the sequence of the epitope, does not occur in the natural (or wild type or native) sequence of the therapeutic protein or the viral vector protein as used in the state of the art therapy. The invention does not envisage fusion proteins wherein an existing epitope within the protein is repeated as a fusion partner of the protein. The invention does not envisage proteins wherein the above defined epitope of a) would be an existing epitope which is excised from the sequence of the protein and inserted at another part of the proteins by deletion and insertion via recombinant DNA technology.

In embodiments of these kits the protein of b) is a fusion protein comprising as fusion partners:
b1) a therapeutic protein or a viral vector protein and
b2) the epitope defined in a1), wherein the epitope sequence is a sequence which differs from the sequence of the protein of b1).

In embodiments of these kits the oxidoreductase motif sequence is C-X(2)-C [SEQ ID NO: 2].

In embodiments of these kits CD1d-restricted NKT cell epitope motif has the sequence [FWYHT]-X(2)-[VILM]-X(2)-[FWYHT] [SEQ ID NO: 1].

In embodiments of these kits the CD1d-restricted NKT cell epitope motif has the sequence [FWY]-X(2)-[VILM]-X(2)-[FWY] [SEQ ID NO:28].

In embodiments of these kits said MHC class II T cell epitope is a promiscuous epitope binding to one or more HLA-DR1 molecules.

In embodiments of these kits the MHC class II T cell epitope has the sequence X1X2MATX6LLM [SEQ ID NO: 29], wherein X1 and X2 are independently selected from V, I, L, M, Y, H, F and W, and X6 is R or P.

An aspect of the invention relates to the above kits for use as a medicament.

An aspect of the invention relates to polypeptides comprising:
b1) a therapeutic protein, and
b2) an MHC class II T cell epitope or a CD1d-restricted NKT cell peptide epitope, wherein the epitope sequence is a sequence which differs from the sequence of the protein of b1.

for use as a medicament in an individual who has been previously treated with a peptide comprising:
a1) said MHC class II T cell epitope or said CD1d-restricted NKT cell epitope and
a2) immediately adjacent to said epitope or separated by at most 7 amino acids from said epitope a sequence with a [CST]-X(2)-C [SEQ ID NO:7] or C-X(2)-[CST] [SEQ ID NO:8] oxidoreductase motif sequence.

An aspect of the invention relates to expression vectors encoding a polypeptide comprising:
b1) a therapeutic protein, and
b2) an MHC class II T cell epitope or a CD1d-restricted NKT cell peptide epitope, wherein the epitope sequence is a sequence which differs from the sequence of the protein of b1.

for use as a medicament in an individual who has been previously treated with a peptide comprising:
a1) said MHC class II T cell epitope or said CD1d-restricted NKT cell epitope and
a2) immediately adjacent to said epitope or separated by at most 7 amino acids from said epitope a sequence with a [CST]-X(2)-C [SEQ ID NO:7] or C-X(2)-[CST] [SEQ ID NO:8] oxidoreductase motif sequence.

An aspect of the invention relates to viral vectors for gene therapy or gene vaccination comprising in the backbone a polynucleotide sequence encoding a protein comprising:
b1) a viral protein for the function and maintenance of the vector, and
b2) an MHC class II T cell epitope or a CD1d-restricted NKT cell epitope, wherein the epitope sequence is a sequence which differs from the sequence of the protein of b1, for use as a medicament in an individual who has been previously treated with a peptide comprising:
a1) said MHC class II T cell epitope or said CD1d-restricted NKT cell epitope and
a2) immediately adjacent to said epitope or separated by at most 7 amino acids from said epitope a sequence with a [CST]-X(2)-C [SEQ ID NO:7] or C-X(2)-[CST] [SEQ ID NO:8] oxidoreductase motif sequence An aspect of the invention relates to a peptide comprising:
a1) an MHC class II T cell epitope or a CD1d-restricted NKT cell peptide epitope, and
a2) immediately adjacent to said epitope or separated from said epitope by at most 7 amino acids a sequence with a [CST]-X(2)-C [SEQ ID NO:7] or C-X(2)-[CST] [SEQ ID NO:8] oxidoreductase motif sequence, for preventing an immune response against a therapeutic protein or against a viral vector protein with said MHC class II T cell epitope or said CD1d binding peptide epitope,
wherein said epitope has a sequence which does not occur in the sequence of the therapeutic protein or of the viral vector protein.

An aspect of the invention relates to methods for preparing kits of parts of polypeptides, comprising a) preparing a modified therapeutic protein by introducing into the sequence of said protein the sequence of an MHC class II T cell epitope or a CD1d-restricted NKT cell epitope, which epitope sequence is a sequence which does not occur in the unmodified protein, b) preparing a peptide comprising:
the MHC class II T cell epitope or a CD1d-restricted NKT cell peptide epitope of a), and
immediately adjacent to said epitope or separated by at most 7 amino acids from said epitope a [CST]-X(2)-C [SEQ ID NO:7] or C-X(2)-[CST] [SEQ ID NO:8] oxidoreductase motif sequence.

An aspect of the invention relates to methods for preparing kits of parts, comprising a) preparing a vector comprising a polynucleotide sequence encoding a modified therapeutic protein or a modified viral vector protein for the function and maintenance of the vector by introducing into the sequence of said proteins the sequence of an MHC class II T cell epitope or a CD1d-restricted NKT cell peptide epitope, which epitope sequence is a sequence which does not occur in the unmodified protein, b) preparing a peptide comprising:
the MHC class II T cell epitope or a CD1d-restricted NKT cell peptide epitope of a), and
immediately adjacent to said epitope or separated by at most 7 amino acids from said epitope a [CST]-X(2)-C [SEQ ID NO:7] or C-X(2)-[CST] [SEQ ID NO:8] oxidoreductase motif sequence.

An aspect of the invention relates to peptides with a length of between 12 and 100 amino acids comprising:
a modified CLIP sequence with motif X1X2MATX6LLM [SEQ ID NO:29], wherein X1 and X2 are independently selected from V, I, L, M, F, H, Y and W, and wherein X6 is R or P, and
immediately adjacent to said modified CLIP sequence or separated by at most 7 amino acids from said modified CLIP sequence a [CST]-X(2)-C [SEQ ID NO:7] or C-X(2)-[CST] [SEQ ID NO:8] oxidoreductase motif sequence.

In embodiments hereof the CLIP sequence is selected from the group consisting of FFMATRLLM [SEQ ID NO:30], WWMATRLLM [SEQ ID NO:31], WFMATRLLM [SEQ ID NO:32], FWMATRLLM [SEQ ID NO:33], FFMATPLLM [SEQ ID NO:34], WWMATPLLM [SEQ ID NO:35], WFMATPLLM [SEQ ID NO:36] and FWMATPLLM [SEQ ID NO:37].

An aspect of the invention relates to therapeutic proteins or polynucleotides encoding a therapeutic protein or encoding a viral vector protein, characterised in the presence of an MHC class II T cell epitope, which epitope has a sequence which does not occur in the sequence of the therapeutic protein or of the viral vector protein wherein said MHC class II T cell epitope has a sequence with motif X1X2MATX6LLM [SEQ ID NO:29], wherein X1 and X2 are independently selected from V, I, L, M, F, H, Y and W, and wherein X6 is R or P.

An aspect of the invention relates to expression vectors comprising a multiple cloning site for the in frame insertion of a polynucleotide encoding a therapeutic protein, characterised in the presence of a nucleotide sequence encoding a promiscuous MHC class II T cell epitope or a CD1d-restricted NKT cell epitope, such that upon insertion of said polynucleotide of said therapeutic protein in said expression vector, a fusion protein is encoded and expressed comprising said therapeutic protein fused to said promiscuous MHC class II T cell epitope or said CD1d-restricted NKT cell epitope.

In embodiments hereof the expression vector is a mammalian expression vector.

In embodiments the expression vector comprises a sequence encoding a therapeutic protein in frame with a sequence encoding a promiscuous MHC class II T cell epitope or a CD1d-restricted NKT cell epitope, under the control of transcription and translation elements, allowing the expression of a fusion protein comprising said therapeutic protein fused to said promiscuous MHC class II T cell epitope or said CD1d-restricted NKT cell epitope, wherein said epitope has a sequence which differs from the sequence of the therapeutic protein.

In certain embodiments the MHC class II T cell epitope has a sequence with motif X1X2MATX6LLM [SEQ ID NO:29], wherein X1 and X2 are independently selected from V, I, L, M, F, H, Y and W, and wherein X6 is R or P.

In embodiments hereof the sequence is selected from the group consisting of FFMATRLLM [SEQ ID NO:30], WWMATRLLM [SEQ ID NO:31], WFMATRLLM [SEQ ID NO:32], FWMATRLLM [SEQ ID NO:33], FFMATPLLM [SEQ ID NO:34], WWMATPLLM [SEQ ID NO:35], WFMATPLLM [SEQ ID NO:36] and FWMATPLLM [SEQ ID NO:37].

The invention relates to combinations of polypeptides of:
a) a modified therapeutic protein or a modified viral vector protein characterised in that the modification is the presence of an MHC class II T cell epitope or an CD1d-restricted NKT cell peptide epitope, which epitope has a sequence which does not occur in the unmodified sequence of the therapeutic protein or of the viral vector protein, and
b) a peptide comprising the MHC class II T cell epitope or the CD1d-restricted NKT cell peptide epitope defined in a) and immediately adjacent to the epitope or separated by at most 7 amino acids from the epitope a sequence with a [CST]-X(2)-C [SEQ ID NO:7] or C-X(2)-[CST] [SEQ ID NO:8] oxidoreductase motif sequence.

In embodiments of the combinations, the protein in a) is a fusion protein of the therapeutic protein or of the viral vector protein fused to an MHC class II T cell epitope or an CD1d-restricted NKT cell peptide epitope.

In embodiments of the combinations, the protein in a) is modified with at least 2 different epitopes, and in b) at least 2 peptides are present, each peptide comprising an epitope as defined in a).

In embodiments of the combinations, the oxidoreductase motif sequence is C-X(2)-C [SEQ ID NO:2].

In embodiments of the combinations, in b) the epitope and the redox motif are separated by at most 4 amino acids.

Embodiments of the CD1d-restricted NKT cell peptide epitope motif are [FWYHT]-X(2)-[VILM]-X(2)-[FWYHT] [SEQ ID NO:1], or [FWYH]-X(2)-[VILM]-X(2)-[FWYH] [SEQ ID NO:27] and [FWY]-X(2)-[VILM]-X(2)-[FWY] [SEQ ID NO:28].

In a typical embodiment, the T cell epitope is a promiscuous epitope binding to one or more HLA-DR1 molecules, which preferably binds to at least HLA-DR1*0101, HLA-DR1'0102, and HLA-DR1*0302.

In specific embodiments, the T cell epitope has the sequence $\underline{X_1X_2}MAT\underline{X_6}$ LLM [SEQ ID NO:29], wherein $X_1$ and $X_2$ are independently selected from V, I, L, M, Y, H, F and W, and $X_6$ is R or P. Examples hereof are FFMAT$\underline{R}$LLM

[SEQ ID NO:30], WWMATRLLM[SEQ ID NO:31], WFMATRLLM [SEQ ID NO:32], or FWMATRLLM [SEQ ID NO:33].

The invention relates to the combination of polypeptides described in the above aspect for use as a medicament.

The invention relates to modified therapeutic protein or a modified viral vector protein wherein the modification is the presence of an MHC class II T cell epitope or a CD1d-restricted NKT cell peptide epitope, which epitope has a sequence which does not occur in the unmodified sequence of the therapeutic protein or of the viral vector protein, for use as a medicament in an individual who has been previously treated with a peptide comprising the MHC class II T cell epitope or the CD1d-restricted NKT cell peptide epitope and immediately adjacent to the epitope or separated by at most 7 amino acids from the epitope a sequence with a [CST]-X(2)-C [SEQ ID NO:7] or C-X(2)-[CST] [SEQ ID NO:8] oxidoreductase motif sequence.

The invention relates to a peptide comprising an MHC class II T cell epitope or a CD1 d binding peptide epitope and comprising immediately adjacent to the epitope or separated by at most 7 amino acids from the epitope a sequence with a [CST]-X(2)-C [SEQ ID NO:7] or C-X(2)-[CST] [SEQ ID NO:8] oxidoreductase motif sequence, for preventing an immune response against a therapeutic protein or against a viral vector protein with the MHC class II T cell epitope or the CD1d binding peptide epitope,
  wherein the epitope has a sequence which does not occur in the wild type sequence of therapeutic protein or the viral vector protein, and optionally
- wherein the protein does not contain a sequence with a [CST]-X(2)-C [SEQ ID NO:7] or C-X(2)-[CST] [SEQ ID NO:8] in the 7 amino sequence at the N terminal or C terminal part of the epitope sequence.

The invention relates to methods for preparing a modified therapeutic protein or a modified viral vector protein comprising the step of introducing into the sequence of the protein the sequence of an MHC class II T cell epitope or a CD1d-restricted NKT cell peptide epitope, which is a sequence which does not occur in the unmodified protein.

Typically, the epitope sequence is attached to the protein to obtain a fusion protein. The invention relates to peptides with a length of between 12 and 100 amino acids comprising a modified CLIP sequence with motif $X_1X_2$MAT$X_6$LLM [SEQ ID NO:29], wherein $X_1$ and $X_2$ are independently selected from V, I, L, M, F, H, Y and W, and wherein $X_6$ is R or P. Examples hereof are FFMATRLLM [SEQ ID NO:30], WWMATRLLM [SEQ ID NO:31], WFMATRLLM [SEQ ID NO:32], FWMATRLLM [SEQ ID NO:33], FFMATPLLM [SEQ ID NO:34], WWMATPLLM [SEQ ID NO:35], WFMATPLLM [SEQ ID NO:36] and FWMATPLLM [SEQ ID NO:37].

In specific embodiments, these peptides further comprise a sequence with a [CST]-X(2)-C [SEQ ID NO:7] or C-X(2)-[CST] [SEQ ID NO:8] redox motif sequence, wherein the redox motif sequence and the modified clip sequence are separated by 0 to 7 amino acids, or 0 to 4 amino acids, or 0 to 2 amino acids.

A specific embodiment of the motif is C-X(2)-C [SEQ ID NO:2].

The invention relates to modified therapeutic proteins or a modified viral vector proteins characterised in that the modification is the presence of an MHC class II T cell epitope or an CD1d-restricted NKT cell peptide epitope, which epitope has a sequence which does not occur in the unmodified sequence of the therapeutic protein or of the viral vector protein.

DETAILED DESCRIPTION

Definitions

The distinction between the term "peptide" and "protein" is arbitrarily since both refer to polypeptides connected by peptide bonds, but which can comprise non-amino acid structures (like for example a linking organic compound). Polypeptides can contain any of the conventional 20 amino acids or modified versions thereof as obtained with post-translational modifications, or can contain non-naturally occurring amino-acids incorporated by chemical peptide synthesis or by chemical or enzymatic modification (e.g. physiological amino acids). As used herein peptide will be used to refer to a molecule comprising an amino acid sequence of between 2 up to 20, 30, 50, 75 or 100 amino acids.

The term "antigen" as used herein refers to a structure of a macromolecule, typically a protein (with or without polysaccharides) or a proteic composition comprising one or more hapten (s), and comprising T cell epitopes. The term "antigenic protein" as used herein refers to a protein comprising one or more T cell epitopes. An auto-antigen or auto-antigenic protein as used herein refers to a human or animal protein present in the body, which elicits an immune response within the same human or animal body.

The term "food or pharmaceutical antigenic protein" refers to an antigenic protein in a food or pharmaceutical product, such as in a vaccine.

The term "epitope" refers to one or several portions (which may define a conformational epitope) of an antigenic protein which is/are specifically recognised and bound by an antibody or a portion thereof (Fab', Fab2', etc.) or a receptor presented at the cell surface of a B or T cell lymphocyte, and which is able, by this binding, to induce an immune response.

The term "T cell epitope" in the context of the present invention refers to a dominant, sub-dominant or minor T cell epitope, i.e. a part of an antigenic protein that is specifically recognised and bound by a receptor at the cell surface of a T lymphocyte. Whether an epitope is dominant, sub-dominant or minor depends on the immune reaction elicited against the epitope. Dominance depends on the frequency at which such epitopes are recognised by T cells and are able to activate them, among all the possible T cell epitopes of a protein. A T cell epitope is an epitope recognised by MHC class II molecules, which consists of a sequence of typically 9 amino acids which fit in the groove of the MHC II molecule (the length of the peptide fitting in the groove of the MHC II molecule may be 8 or 10 amino acids for some peptide/MHCII complexes). Within a peptide sequence representing a 9 amino acid T cell epitope, the amino acids in the epitope are numbered P1 to P9, amino acids N-terminal of the epitope are numbered P-1, P-2 and so on, amino acids C terminal of the epitope are numbered P+1, P+2 and so on.

"Motifs" of amino acid sequences are written herein according to the format of Prosite (Sigrist et al. (2002) *Brief Bioinform.* 3, 265-274). The symbol X is used for a position where any amino acid is accepted. Alternatives are indicated by listing the acceptable amino acids for a given position, between square brackets ('[ ]'). For example: [CST] stands for an amino acid selected from Cys, Ser or Thr. Amino acids which are excluded as alternatives are indicated by listing them between curly brackets ('{ }'). For example: {AM} stands for any amino acid except Ala and Met. The different elements in a motif are separated from each other by a hyphen -. Repetition of an identical element within a motif can be indicated by placing behind that element a numerical value or a numerical range between parentheses. For example: X(2) corresponds to X-X, X(2,3) corresponds to X-X or X-X-X, A(3) corresponds to A-A-A.

The term "CD1d-restricted NKT cell peptide epitope" or "CD1d-restricted NKT cell peptide epitope" refers to a part of an antigenic protein that is specifically bound by a CD1d molecule, expressed at cell surface and recognized by a NKT cell. The word "peptide" in this definition may be used to emphasise the difference with prior art binding CD1d binding compounds such as ceramides.

The CD1d-restricted NKT cell peptide epitope has a general motif [FWYHT]-X(2)-[VILM]-X(2)-[FWYHT] [SEQ ID NO:1]. Alternative versions of this general motif have at position 1 and/or position 7 the alternatives [FWYH].

Alternative versions of this general motif have at position 1 and/or position 7 the alternatives [FWYT].

Alternative versions of this general motif have at position 1 and/or position 7 the alternatives [FWY].

Regardless of the amino acids at position 1 and/or 7, alternative versions of the general motif have at position 4 the alternatives [ILM].

The term "homologue" as used herein with reference to epitopes used in the context of the invention, refer to molecules having at least 50%, at least 70%, at least 80%, at least 90%, at least 95% or at least 98% amino acid sequence identity with a naturally occurring epitope, thereby maintaining the ability of the epitope to bind an antibody or cell surface receptor of a B and/or T cell. Specific homologues of an epitope correspond to a natural epitope modified in at most three, more particularly in at most 2, most particularly in one amino acid.

The term "derivative" as used herein with reference to peptides of the invention refers to molecules which contain at least the peptide active portion (i.e. capable of detecting CD4+ T cell) and, in addition thereto comprises an additional part which can have different purposes such as stabilising a peptide or altering the pharmacokinetic or pharmacodynamic properties of the peptide.

The term "sequence identity" of two sequences as used herein relates to the number of positions with identical nucleotides or amino acids divided by the number of nucleotides or amino acids in the shorter of the sequences, when the two sequences are aligned. The sequence identity can be more than 70%, more than 80% more than 90% more than 95% more than 98%, or more than 99%.

The terms "peptide-encoding polynucleotide (or nucleic acid)" and "polynucleotide (or nucleic acid) encoding peptide" as used herein refer to a nucleotide sequence, which, when expressed in an appropriate environment, results in the generation of the relevant peptide sequence or a derivative or homologue thereof. Such polynucleotides or nucleic acids include the normal sequences encoding the peptide, as well as derivatives and fragments of these nucleic acids capable of expressing a peptide with the required activity. For example, the nucleic acid encoding a peptide fragment thereof is a sequence encoding the peptide or fragment thereof originating from a mammal or corresponding to a mammalian, most particularly a human peptide fragment.

The term "organic compound having a reducing activity" refers in the context of this invention to compounds, more in particular amino acid sequences, with a reducing activity for disulfide bonds on proteins.

The reducing activity of an organic compound can be assayed for its ability to reduce a sulfhydryl group such as in the insulin solubility assay wherein the solubility of insulin is altered upon reduction, or with a fluorescence-labelled insulin. The reducing organic compound may be coupled at the amino-terminus side of the T-cell epitope or at the carboxy-terminus of the T-cell epitope. Generally the organic compound with reducing activity is a peptide sequence. Peptide fragments with reducing activity are encountered in thioreductases which are small disulfide reducing enzymes including glutaredoxins, nucleoredoxins, thioredoxins and other thiol/disulfide oxydoreductases (Holmgren (2000) *Antioxid. Redox Signal.* 2, 811-820; Jacquot et al. (2002) *Biochem. Pharm.* 64, 1065-1069). They are multifunctional, ubiquitous and found in many prokaryotes and eukaryotes. They exert a reducing activity for disulfide bonds on proteins (such as enzymes) through redox active cysteines within conserved active domain consensus sequences: C-X(2)-C [SEQ ID NO:2], C-X(2)-S [SEQ ID NO:3], C-X(2)-T [SEQ ID NO:4], S-X(2)-C [SEQ ID NO:5], T-X(2)-C [SEQ ID NO: 6] (Fomenko et al. (2003) *Biochem.* 42, 11214-11225; Fomenko et al. (2002) *Prot. Science* 11, 2285-2296), in which X stands for any amino acid. Such domains are also found in larger proteins such as protein disulfide isomerase (PDI) and phosphoinositide-specific phospholipase C.

The term "natural" "wild type", "native" when referring to a peptide or a sequence herein relates to the fact that the sequence is identical to a naturally occurring sequence or a fragment thereof. In contrast therewith the term "artificial" refers to a sequence or peptide which as such does not occur in nature and differs from the above natural/wild type/native sequence. Optionally, an artificial sequence is obtained from a natural sequence by limited modifications such as changing one or more amino acids within the naturally occurring sequence or by adding amino acids N- or C-terminally of a naturally occurring sequence. Amino acids are referred to herein with their full name, their three-letter abbreviation or their one letter abbreviation. An artificial sequence can also be obtained by chemically modifying amino acid side chains or by including non-natural amino acids.

The term "major histocompatibility antigen" refers to molecules belonging to the HLA system in man (H2 in the mouse), which are divided in two general classes. MHC class I molecules are made of a single polymorphic chain containing 3 domains (alpha 1, 2 and 3), which associates with beta 2 microglobulin at cell surface. Class I molecules are encoded by 3 loci, called A, B and C in humans. Such molecules present peptides to T lymphocytes of the CD8+ subset. Class II molecules are made of 2 polymorphic chains, each containing 2 chains (alpha 1 and 2, and beta 1 and 2). These class II molecules are encoded by 3 loci, DP, DO and DR in man. Hereof the HLA-DR molecule is the most prevalent in humans. The frequency of alleles in different nationalities and ethnic can be obtained from allelefrequencies.net (Gonzalez-Galarza et al. (2015) Nucl. Acid Res. 28, D784-D788.

"Gene therapy" can be defined as the insertion, ex vivo or in vivo, of a gene or genes into individual cells or groups of cells (such as tissues or organs) with the purpose to provide a missing gene or allele or to replace a mutant gene or a mutant allele with a functional copy delivered by the gene therapy. The "therapeutic gene" is delivered via a carrier called a vector. The most common vector is a viral vector. Upon infection of targeted cells with the viral vector carrying the therapeutic gene, the viral vector unloads its genetic material including the therapeutic gene into the target cells, followed by the generation of the functional protein(s) encoded by the therapeutic gene. Cells targeted by gene therapy can be either somatic cells or germ cells or cell lines.

In addition, gene therapy refers to the use of vectors to deliver, either ex vivo or in vivo, a gene that requires overexpression or ectopic expression in a cell or group of cells. The vector can facilitate integration of the new gene in the nucleus or can lead to episomal expression of that gene.

"Gene vaccination" can be defined as the administration of a functional gene (i.e., capable of expressing the protein encoded by the gene) to a subject for the purpose of vaccinating a subject. Thus, gene vaccination (or DNA vaccination) is a variant of the more classical vaccination with peptides, proteins, attenuated or killed germs, etc. Gene vaccination can be performed with naked DNA or, of particular interest in the context of the present invention, with viral vectors.

The term "viral vector protein" when used herein refers to any protein or peptide derived from the backbone of a viral vector as such and which are required for the function and maintenance of the vector. It does not refer to the therapeutic gene which is cloned into the vector. Typically such viral vector proteins are antigenic and comprise one or more epitopes such as T-cell epitopes. A well-known example is the capsid protein. Several viruses are currently used for gene therapy, both experimental and in man, including RNA viruses (gamma-retroviruses and lentiviruses) and DNA viruses (adenoviruses, adeno-associated viruses, herpes viruses and poxviruses).

The term "allofactor" or "alloantigen" refers to a protein, peptide or factor (i.e., any molecule) displaying polymorphism when compared between 2 individuals of the same species, and, more in general, any protein, peptide or factor that is inducing an (alloreactive) immune response in the subject receiving the allofactor.

The term "alloreactivity" refers to an immune response that is directed towards allelic differences between the graft recipient and the donor. Alloreactivity applies to antibodies and to T cells. The present invention relies entirely on T cell alloreactivity, which is based on T cell recognition of alloantigens presented in the context of MHC determinants as peptide-MHC complexes.

The term "promiscuous" refers to epitopes which carry the property of being able to bind to different MHC class II molecules in order to cover a substantial percentage of the envisaged population. A substantial percentage is at least 50%, or least 60%, at 75%, at least 90% or even at least 95% of the envisaged population.

The envisaged population can be defined as individuals of one or more countries or of one or more regions or continents, or as members of an ethnic group.

Alternatively, a promiscuous epitope can be defined as binding to at least 7, 8, 9 or 10 of the 15 most prevalent HLA DR alleles in the envisaged population.

Promiscuous epitopes can be natural sequences as occurring in an antigen or modified by substitution of one or more amino acids (2, 3 or 4) of a natural sequence occurring in an antigen, or completely artificial, including non-physiological amino acids, amino acids containing modified side chains, or small compounds.

The term "universal epitope" also occurs in the art. However this relates to an epitope sequence which is encountered in different antigens. Such an universal epitope may or may not bind to different MHC molecules and alleles.

One aspect of the present invention relates to modified version of therapeutic proteins or of viral vector proteins with an added MHC class II T cell epitope or with an added CD1d-restricted NKT cell peptide epitope. This is typically done by generating fusion proteins of the antigen and the epitope sequence, although the epitope sequence can be introduced as well in the protein itself.

Herein the 9 amino acid T cell epitope sequence or the 7 amino acid CD1d-restricted NKT cell peptide epitope sequence is not a fragment of the wild type therapeutic protein or of the viral vector protein.

This can be achieved by a modification of an epitope sequence as occurring in the therapeutic protein/viral vector protein, or by the use of an epitope sequence as occurring in another antigen (human or non-human) or by the use of a designed sequence with low or no sequence identity to any existing antigen epitope sequence. The MHC class II T cell epitope can be a promiscuous epitope. The rationale for this choice is explained later on in more detail.

The modified therapeutic protein/viral vector protein could itself elicit the generation of CD4+ cytotoxic cells, if in this protein a [CST]-X(2)-C [SEQ ID NO:7] C-X(2)-[CST][SEQ ID NO:8] motif sequence is within 4, typically within 7 amino acids from the sequence of the introduced class II T cell epitope or the introduced CD1d-restricted NKT cell peptide epitope. This can happen when the modification includes, apart from the introduction of the epitope sequence, also the introduction of a oxidoreductase sequence. In some proteins which contain in their wild type sequence an oxidoreductase sequence, the protein can be engineered to contain the epitope sequence in the proximity (separated by at most 7 or at most 4 amino acids) of the naturally occurring oxidoreductase sequence.

If such activity is not required by the modified therapeutic protein/viral vector protein, the modification is limited to the introduction of the epitope sequence. If the modified therapeutic protein/viral vector protein contains in its wild type sequence an oxidoreductase sequence, the added epitope sequence is introduced in the modified protein such that the added epitope and the existing oxidoreductase motif are separated by at least 4, or at least 7 amino acids.

The epitope can occur in a fusion protein N terminal of the antigen, or C terminal of the antigen, depending on the impact of the added epitope sequence on the function of the protein. In specific embodiments two or more different epitopes are added to the antigen.

If appropriate a linker sequence can be inserted between the epitope sequence and the sequence of the native antigen.

It is also envisaged to generate modified versions of an antigen wherein the epitope sequence is fused internally in the sequence at a region which is not critical for the function of the protein. In alternative embodiments a foreign epitope sequence is generated by mutating and/or adding one or more amino within the sequence of the antigen.

The length of the protein with the introduced epitope sequence (added as a fusion protein, or internal) is mainly defined by the antigen and is not a limiting feature. The antigen can be very small in case of peptide hormones. The impact of mutations within a protein is likely larger in shorter proteins, and encourages to consider fusion proteins for proteins with a length of less than 100 or less than 250 amino acids.

The therapeutic agent of the present invention includes any peptide or protein agent used to compensate for the absence of a physiological agent or to alter, modify, stop or slow down a disease process.

Such therapeutic agents include:
1. replacement agents for coagulation defects, including factor VIII, factor IX and factor X deficiencies, administration of factor VII to correct a deficiency or as a therapeutic agent in trauma, surgery, heart failure or in the treatment of patients affected by haemophilia and producing inhibitory antibodies which preclude administration of the missing factor (factor VIII or factor IX)
2. fibrinolytic agents, including staphylokinase or tissue plasminogen activator (tPA) administered in stroke and cardiac infarction
3. hormones such as growth hormone or insulin to treat nanism and insulin-dependent diabetes mellitus
4. cytokines and growth factors, such as interferon-alpha, interferon-gamma, GM-CSF and G-CSF; cytokine receptors such as IL-6 receptor and IL-1b receptor in the treatment of rheumatoid arthritis
5. antibodies for the modulation of immune responses, including anti-IgE antibodies in allergic diseases, anti-CD3 and anti-CD4 antibodies in graft rejection and a variety of autoimmune diseases, anti-CD20 antibodies in non-Hodgkin lymphomas anti-cytokine or cytokine receptor (e.g. anti-IL6R).

Humanized therapeutic antibodies are human except for the epitope binding site (CDRs), usually derived from a mouse sequence. The present invention aims to eliminate the capacity to mount a response towards the non-human part of the antibody.
6. erythropoietin in renal insufficiency.
7. replacement therapy with enzymes, including alpha-galactosidase A (Fabry disease), beta-glucocerebrase (type 1 Gaucher disease) and alpha-glucosidase (Pompe disease).

Further to the above section on proteins with an added MHC class II T cell epitope or CD1d-restricted NKT cell peptide epitope, another aspect of the present invention relates to a combination of a protein as described above, and another peptide comprising a 4 amino acid oxidoreductase sequence and comprising the same epitope sequence that has been added to the therapeutic protein or the viral vector.

In this peptide, the oxidoreductase sequence has the motif [CST]-X(2)-C [SEQ ID NO:7] or C-X(2)-[CST] [SEQ ID NO:8]. This motif encompasses the alternatives C-X(2)-C [SEQ ID NO:2], S-X(2)-C [SEQ ID NO:5], T-X(2)-C [SEQ ID NO:6], C-X(2)-S [SEQ ID NO:3] and C-X(2)-T [SEQ ID NO:4]. A particular choice of the motif is C-X(2)-C [SEQ ID NO:2].

In the motif of reducing compounds, C represents either cysteine or another amino acids with a thiol group such as mercaptovaline, homocysteine or other natural or non-natural amino acids with a thiol function. In order to have reducing activity, the cysteines present in the motif should not occur as part of a cystine disulfide bridge. The amino acid X in the redox can be any natural amino acid, or can be a non-natural amino acid. X can be an amino acid with a small side chain such as Gly, Ala, Ser or Thr. In particular versions at least one X in the redox motif is His, Pro or Tyr. In particular versions X is not Cys, in other particular versions X is not W, F or Y.

In particular conditions, peptides are provided comprising one epitope sequence and a motif sequence. The motif can occur once or several times (2, 3, 4 or even more times) in the peptide, for example as repeats of the motif which can be spaced from each other by one or more amino acids, as repeats which are adjacent to each other, or as repeats which overlap with each other.

The epitope sequence and the 4 amino acid oxidoreductase sequence do not overlap and are separated by a linker sequence of 7, 6, 5, 4, 3, 2 or 1 amino acids, or are immediately adjacent to each other (thus no linker sequence or linker of 0 amino acids). Typical ranges are a linker of 0 to 2 amino acids, a linker of 0 to 4 amino acids, or a linker of 0-7 amino acids.

When the epitope sequence in the peptide is a fragment of an antigen, the amino acids in the linker are typically the amino acid(s) which flank the epitope in the antigen. Alternatively the amino acids in a linker are Gly and/or Ser.

The redox motif can be as well at the N terminus or at the C terminus of the epitope sequence.

The peptide with redox motif sequence and epitope sequence can be as short as 12 or 13 amino acids for peptides with an MHC class II T cell epitope or 11 amino acids for peptides with a CD1d-restricted NKT cell peptide epitope, up to 20, 30, 40, 50, 75 or 100 amino acids, depending on the number of amino acids between epitope and oxidoreductase motif, and the number of flanking amino acids at N and/or C terminus of the "epitope+linker+redox motif" sequence or "redox motif+linker+epitope" sequence.

Thus depending on the embodiment of choice the epitope is a MHC class II epitope or a CD1d-restricted NKT cell peptide epitope. CD1d-restricted NKT cell peptide epitopes can be used to generate cytolytic CD4+ T cells via NKT cells.

CD1d-restricted NKT cell peptide epitopes have the advantage that they will in all individuals bind to the CD1d binding since there is no polymorphism for this protein.

The use of proteins with an added MHC class II T cell epitope or CD1d-restricted NKT cell peptide epitope in combination with a peptide comprising this epitope and a redox motif allows to uncouple the epitope sequence used to elicit the cytolytic CD4+ cell population from epitope sequences within the antigen itself.

This is especially the case for fusion proteins of a protein fused to an epitope, since this requires no modification to the sequence of the protein itself. Modifying the therapeutic protein to contain the new epitope sequence is a task that has to be optimised for each protein.

Uncoupling the epitope sequence from the antigen sequence allows to design a tailor made epitope sequence. This sequence can be optimised to improve solubility and stability, decrease degradation, and the like. Apart from the choice of certain amino acids in the sequence, other alterations can be envisaged such as the incorporation of non-natural amino acids or D-amino acids during peptide synthesis, or posttranslational modifications such as citrullination, acetylation and sulfatation.

An epitope sequence can also be optimised to assure that the MHC class II T cell epitope will bind to different HLA proteins such that the will be recognised by CD4+ T cells in a large proportion of subjects. Such epitopes are known in the art as promiscuous epitopes.

Examples of such promiscuous epitopes can be found in viral agents such as measles or hepatitis C, mycobacteria, tumor-related viral antigens or even in autologous proteins. Algorithms to determine the binding of an epitope sequence with an HLA molecule or allele, and to identify promiscuous epitopes in a protein sequence are known. Candidate promiscuous epitopes can be tested on different MHC molecules.

As an alternative or in addition to the use of a promiscuous MHC class II T cell epitope, two or more peptides can be mixed for vaccination, each containing a thioreductase motif and MHC class II T cell epitope, so as to cover the largest possible numbers of MHC class II determinants. In this case the antigen will also carry the two or more epitope sequences used in the peptide mixture (typically in the form of a fusion protein).

In a specific embodiment a combination of an MHC Class II T cell epitope and a CD1d-restricted NKT cell peptide epitope is used.

In a specific embodiment, the promiscuous epitope is derived from the CLIP (CLass II associated Invariant chain Peptide (KM$_1$R$_2$MATP$_6$LLMQAL) [SEQ ID NO:9]) sequence obtained by proteolytic cleavage of the invariant chain. CLIP is protecting the hydrophobic peptide-binding groove of MHC class II molecule until it is displaced by competition with a peptide of higher affinity. CLIP protects all nascent MHC class II molecules from the DR, DP or DQ family, and as such is the most illustrative example of a promiscuous epitope. However, the affinity of CLIP for class II molecules is weak, so that there is no presentation of MHC class II molecules with CLIP at the surface of an antigen-presenting cell. The DM protein catalyses the replacement of CLIP by alternative peptides for surface presentation (Pos et al. (2012) *Cell* 151, 1557-1568). It is an aspect of the invention that replacement of the first CLIP amino acid residue located in the P1 pocket of the MHC class II molecule by a hydrophobic residue such as F, W, H or Y or V, I, L, or M is sufficient as to prevent the complete replacement by an alternative peptide and allow presentation of modified CLIP at the surface of an antigen-presenting cell. This results in activation of CD4+ T cells. In an alternative version, also the second amino acid residue of the MHC binding fragment of CLIP is replaced by a hydrophobic residue.

In addition, the proline residue located in position 6 can be mutated from P to R to further increase its binding affinity.

Accordingly the present invention provides peptides comprising a modified version of the MHC class II binding region of the Clip peptide represented by the general sequence motif [VILMFWYH]$_1$[RVILMFWYH]$_2$MAT[PR]$_6$LLM [SEQ ID NO: 10].

In such modified Clip peptides, independent from each other P1, can also be [FWHY] [FWH] or [FW], P2 can be [RFWHY], RFW or R, P6 can be P.

In specific embodiments, P1 and P6 are modified with one of the above possibilities and P2 Arginine is not modified.

Peptides can be made entirely artificially using sequences which fit closely in a majority of MHC class II molecules. One example of this is provided by the PADRE peptide (aKXVAAWTLKAAaZC (a=D-Alanine, X=I-cyclohexyl-alanine, Z=aminocaproic acid) [SEQ ID NO:11] (Alexander et al. (2000) *J. Immunol.* 64, 1625-1633). Such artificial promiscuous peptides can be made from computer algorithms taking into account the properties of the amino acid residues and those of the MHC class II molecules to obtain the best fit. One example of such algorithms is provided by ProPred (Sigh and Raghava (2001), *Bioinformatics* 17, 1236-1237). Other examples of algorithms are given below.

Promiscuous epitopes are also encountered in tetanus toxoid peptide (830-843) or influenza haemagglutinin, HA(307-319).

Methods for the detection of promiscuous epitopes by in silico and cell based assays are described in Mustafa et al. (2014) *PLoS One* 9, e103679; Grzybowska-kowalczyk (2015) *Thorax* 69, 335-345; Grabowska et al. (2014) *Int. J. Cancer* 224, 1-13; Fraser et al. (2014). *Vaccine* 32, 2896-2903.

Non-natural (or modified) T-cell epitopes can further optionally be tested on their binding affinity to MHC class II molecules. This can be performed in different ways. For instance, soluble HLA class II molecules are obtained by lysis of cells homozygous for a given class II molecule. The latter is purified by affinity chromatography. Soluble class II molecules are incubated with a biotin-labelled reference peptide produced according to its strong binding affinity for that class II molecule. Peptides to be assessed for class II binding are then incubated at different concentrations and their capacity to displace the reference peptide from its class II binding is calculated by addition of neutravidin. Methods can be found in for instance Texier et al. (2000) *J. Immunol.* 164, 3177-3184.

Additionally and/or alternatively, one or more in silico algorithms can be used to identify a T cell epitope sequence within a protein. Suitable algorithms include, but are not limited to those found on the following websites:
cvc.dfci.harvard.edu/balbc/;
syfpeithi.de/;
abi.inf.uni-tuebingen.de/Services/SVMHC;
bio.dfci.harvard.edu/Tools/antigenic.html;
ddg-pharmfac.net/mhcpred/MHCPred/;
immunax.dfci.harvard.edu (PEPVAC); and
epivax.com/epimatrix/.

More particularly, such algorithms allow the prediction within an antigenic protein of one or more nonapeptide sequences which will fit into the groove of an MHC II molecule.

An example of determining the promiscuous nature of MHC class II peptides is described in WO2015/033140 using the method developed by Stumiolo et al. (1999) *Nat. Biotechnol.* 17, 555-561) available at www.iedb.org. Herein HLA Class II alleles considered for the analysis are HLA-DRA*01:01/HLA-DRB1*01:01, DRA*01:01/HLA-DRB1*03:01, DRA*01:01/HLA-DRB1*04:01, DRA*01:01/HLA-DRB1*07:01, DRA*01:01/HLA-DRB1*08:02, DRA*01:01/HLA-DRB1*11:01, DRA*01:01/HLA-DRB1*13:01 and DRA*01:01/HLA-DRB1*15:01 respectively considered as representative members of HLA-DR1, HLA-DR3, HLA-DR4, HLA-DR7, HLA-DR8, HLA-DR11, HLA-DR13 and HLA-DR15 antigen groups.

It is a further aspect of the present invention that class II-restricted epitopes, be them natural or artificial, can be used as a vaccine to elicit cytolytic CD4+ T cells. Subsequent administration of a therapeutic protein to which the same epitope, but without thioreductase motif, is added leads to activation of cytolytic CD4+ T cells obtained by vaccination. This results in the prevention of an immune response to the therapeutic agent.

The methods of the present invention relate to combination therapies wherein a peptide with a redox motif and a T cell epitope or a CD1d-restricted NKT cell peptide epitope are used to generate a population of cytotoxic CD4+ T cells, or cytotoxic CD4+ NKT cells, respectively, which kill antigen-presenting cells presenting an antigen which contains the epitope sequence used in the peptide with redox motif. In this way a subject is vaccinated and an immune response against a later administered antigenic protein with the epitope is prevented.

The use of promiscuous class II-restricted T cell epitopes and CD1d binding peptide epitopes for vaccination before administration of therapeutic agents are therefore an aspect of the present invention. The use of therapeutic agents containing the same epitope as that used for vaccination but without thioredox motif are a part of this aspect of the invention.

Peptides and therapeutic agents are used to treat subjects in need of the therapeutic agent. Thus, in one application of the invention the subject is immunized with a peptide encompassing a promiscuous epitope and a thioreductase motif. Typically, such immunization is carried out by subcutaneous administration of a peptide adsorbed or dissolved in an adjuvant. The immunized subject is then treated with the therapeutic agent for which he/she is in need, the agent containing the same promiscuous epitope as the one included in the peptide used for vaccination, but without the thioreductase motif. The immune response towards the therapeutic agent is prevented due to the vaccination procedure through which cytolytic CD4+ T cells specific for the promiscuous epitope have been elicited.

Administration of the peptide containing a thioredox motif can be carried out by direct immunization. Alternatively, administration may consist in cells obtained from the subject in need for a therapeutic agent, exposure of cells to the peptide in vitro for eliciting and expanding cytolytic CD4+ T cells and re-administration to a subject.

T cell epitopes of the present invention are thought to exert their properties by increasing the strength of synapse formation by creating a disulfide bridge between the thioreductase motif and the CD4 molecule. This mechanism of action is substantiated by experimental data (see examples below), but there is no intention to restrict the present invention to this specific mechanism of action.

It should be obvious for those skilled in the art that multiple variations of this sequence of events can be delineated, depending on the type and frequency at which the therapeutic agent has to be administered and the clinical condition of the subject in need for a therapeutic agent.

In one of these variations it might be more appropriate to treat the subject first by an infusion of his/her own cells after exposure of such cells to the epitope containing the thioreductase motif in an in vitro cell culture. This could be a preferred method in subjects under immunosuppressive treatment, which would prevent the development of an immune response to the peptide administered with an adjuvant. Peptide administration can be envisaged by any route, with a preferred route being subcutaneous.

Peptides can be made by chemical synthesis, which allows the incorporation of non-natural amino acids and/or of chemically-modified amino acids. Examples of chemically-modified amino acids are encountered in pathological conditions, e.g. glycosylation and citrullination of epitopes in rheumatoid arthritis, deamidation in celiac disease and formation of an intra-epitope disulfide bridge in insulin-dependent diabetes mellitus. However, there are numerous possibilities of modifying amino acid side chains and the above examples are not meant to be exhaustive.

Polypeptides can be generated using recombinant DNA techniques, in bacteria, yeast, insect cells, plant cells or mammalian cells. Peptides of a shorter length can be prepared by chemical peptide synthesis, wherein peptides are prepared by coupling the different amino acids to each other. Chemical synthesis is particularly suitable for the inclusion of e.g. D-amino acids, amino acids with non-naturally occurring side chains or natural amino acids with modified side chains such as methylated cysteine.

Chemical peptide synthesis methods are well described and peptides can be ordered from companies such as Applied Biosystems and other companies. Peptide synthesis can be performed as either solid phase peptide synthesis (SPPS) or contrary to solution phase peptide synthesis. The best-known SPPS methods are t-Boc and Fmoc solid phase chemistry. During peptide synthesis several protecting groups are used. For example hydroxyl and carboxyl functionalities are protected by t-butyl group, lysine and tryptophan are protected by t-Boc group, and asparagine, glutamine, cysteine and histidine are protected by trityl group, and arginine is protected by the pbf group. In certain situations, such protecting groups can be left on the peptide after synthesis.

Alternatively, peptides can be synthesised by using nucleic acid molecules which encode the peptides of this invention in an appropriate expression vector which include the encoding nucleotide sequences. Such DNA molecules may be readily prepared using an automated DNA synthesiser and the well-known codon-amino acid relationship of the genetic code. Such a DNA molecule also may be obtained as genomic DNA or as cDNA using oligonucleotide probes and conventional hybridisation methodologies. Such DNA molecules may be incorporated into expression vectors, including plasmids, which are adapted for the expression of the DNA and production of the polypeptide in a suitable host such as bacterium, e.g. *Escherichia coli*, yeast cell, animal cell or plant cell.

In embodiments of the present invention, expression vectors are provided wherein an MHC class II epitope or CD1d-restricted NKT cell peptide is cloned into the vector, typically upstream or downstream of the multiple cloning of a commercially available expression vector. The in frame insertion of the DNA encoding for a therapeutic protein allows the expression of an epitope tagged protein, comparable to e.g. an His tagged protein or HA tagged protein. Such modified expression vectors can be generated using standard molecular biology techniques.

The attachment of the epitope tag results in a fusion protein of the epitope with a therapeutic protein of choice for replacement therapy. A single vector can be used for any therapeutic protein.

In order to administer the protein to a patient, the protein can be expressed using a bacterial, yeast, plant or mammalian vector. The choice for the type of expression system depends from protein to protein is known for most therapeutic proteins. The isolated protein is accordingly injection.

Alternative, DNA encoding the therapeutic protein fused to the epitope is cloned into a mammalian expression vector suitable for gene therapy in humans.

The physical and chemical properties of a peptide of interest (e.g. solubility, stability) are examined to determine whether the peptide is/would be suitable for use for applications as defined for the present invention. Typically this is optimised by adjusting the sequence of the peptide. Optionally, the peptide can be modified after synthesis (chemical modifications e.g. adding/deleting functional groups) using techniques known in the art. Optionally, peptides can be modified by posttranslational alteration. Examples of this are acetylation, sulfation, citrullination or phosphorylation of single of multiple amino acid residues.

The invention is now illustrated by the following examples, with no intention to restrict the invention to these examples.

Example 1: Therapeutic Antibody

Many viruses contain universal class II restricted T cell epitopes, one example being the hepatitis C virus. The peptide sequences 1247 to 1261

(QGYK VLVLNPSVAA T) [SEQ ID NO: 12]

and 1535 to 1550

(TTVRLRA YMNTPGLPV), [SEQ ID NO: 13]

cover together more 12 of the 15 DRB haplotypes, representative of more than 85% of the general population.

A vaccination strategy making use of a mixture of two peptides encompassing the minimal binding sequence of class II-restricted epitopes and a thioreductase motif is therefore established.

Peptide 1247-1261 contains an MHC class II binding sequence at position 1251-1260 (underlined in SEQ ID NO:12].

Peptide 1535-1550 contains a minimal MHC class II binding sequence at positions 1542-1550 (underlined in SEQ ID NO:13].

Two peptides are prepared for vaccination wherein redox motif and epitope sequence are separated by a VR dipeptide linker:

CPYC-VR-VLVLNPSVAA, [SEQ ID NO: 14]
and

CPYC-VR-YMNTPGLPV [SEQ ID NO: 15]

Administration of a mixture of these two peptides adsorbed on aluminum hydroxide elicits specific CD4+ T cells with cytolytic properties.

Antibodies to CD20 are a recognized treatment for non-Hodgkin lymphoma. However, in a significant percentage of patients, this administration elicits specific antibodies which either preclude further administration or minimize efficacy.

The present invention provides a vaccination strategy to prevent such unwanted immunization.

The above 2 sequences from the hepatitis C virus, namely SEQ ID NO:12 and SEQ ID NO:13, are produced in line with the anti-CD20 antibody and positioned at the amino-terminal end of the heavy chain [SEQ ID NO:16]. Upon administration of this anti-CD20 antibody, cytolytic CD4+ T cells elicited previously by vaccination become activated and eliminate by apoptosis the presentation of determinants from the therapeutic antibody, thereby preventing immunization towards anti-CD20.

Example 2: Erythropoietin

Erythropoietin (EPO) is a 166 amino acid residues long polypeptide, which is the primary mediator of hypoxic induction of erythropoiesis, which in adulthood is produced by the kidney (±80%). Hypoxia induces an increase in EPO production, which then circulates in the plasma and binds to receptors expressed on erythroid progenitor cells, leading to terminal differentiation of such precursors and increase in red blood mass.

Although human recombinant EPO is a weak immunogen, its repetitive use in, for instance, renal insufficiency, subtle differences in glycosylation or in the preparation procedure can lead to the development of specific neutralizing antibodies. As EPO is the sole mediator of erythropoiesis due to hypoxia, the presence of a neutralizing immune response is considered as a dramatic event.

One way to prevent occurrence of such unwanted immune response is to vaccinate individuals in need for EPO with a promiscuous class II restricted T cell epitope linked to a thioreductase motif located within the epitope flanking region. This elicits epitope-specific CD4+ T cells with cytolytic properties. Administration of a molecule of EPO coupled to the same promiscuous epitope activates cytolytic CD4+ T cells, which eliminate by apoptosis antigen-presenting cells presenting EPO and thereby the capacity to mount an immune response to EPO.

The invariant chain contains a CLIP sequence which is a promiscuous T cell epitope, which binds to nascent MHC class II molecules with a relatively low affinity. CLIP is released from its class II binding by competition with peptides showing higher affinity. During this exchange of epitopes, the DM molecule protects the first anchoring pocket of class II molecules in a transient status between CLIP and the new peptide.

A mutated version of CLIP in which the first 2 amino acids, which show weak affinity for class II binding, are replaced by two hydrophobic residues will maintain its promiscuity while increasing affinity for class II molecules. In addition, the residue located in position 6 can be mutated from P to R to further increase its binding affinity. Thus, the sequence KM$_1$R$_2$MATP$_6$LLMQAL [SEQ ID NO:9], in which the second and third amino acid (M and R, respectively) are located in position 1 and 2, respectively, are mutated, as well as P in position 6 to give KF$_1$F$_2$MAT R$_6$LLMQAL [SEQ ID NO:17].

A peptide is generated by addition of a thioreductase motif and a Val Arg linker sequence at the N terminal, giving the full sequence: CPYC-VR-FFMATRLLMQAL [SEQ ID NO:18].

Patients in need for EPO injection are vaccinated by administration of peptide [SEQ ID NO:18] using a standard procedure of peptide adsorbed on aluminum hydroxide and administered by SC injection. This procedure is known to elicit epitope-specific cytolytic CD4+ T cells, as described in patent application WO200817517.

The sequence KFFMATRLLMQAL [SEQ ID NO:17] is added at the terminal end of EPO, separated by two glycines from the EPO sequence, making a total of 181 amino acids. This modified EPO [SEQ ID NO:19] retains its full activity upon administration and activates the cytolytic CD4+ T cells obtained by vaccination, thereby precluding any detrimental immune response.

The promiscuous nature of the CLIP-modified epitope makes it possible to use the same vaccine and the same EPO molecule for any patient in need of such therapy.

Example 3: Alpha-Galactosidase

Fabry disease is lysosomal storage disease with accumulation of glycosphingolipids in various tissues due to absence of alpha-galactosidase, a lysosomal hydrolase. It is a X-linked gene defect disease affecting ±1 out 100,000 individuals. Current therapy of Fabry disease includes regular infusion of alpha-galactosidase. However, more than 25% of patients under such a therapy develop an immune response to the enzyme, preventing any further use of such enzyme and precipitating patients into risks of various complications, including stroke.

Recombinant alpha-galactosidase can be modified as to contain the sequence of a class II-restricted promiscuous T cell epitope added at the amino-terminal end of the molecule. Administration of this modified alpha-galactosidase molecule to individuals previously vaccinated to this promiscuous epitope containing a thioreductase motif, thereby eliciting the production of peptide-specific cytolytic CD4+ T cells, does not elicit an immune response to alpha-galactosidase.

A promiscuous epitope of apolipoprotein B-100 of sequence LFLKSDGRVKYTLN [SEQ ID NO:20] corresponding to amino acids 1277 to 1290, in which P1 is occupied by L1279 (underlined) is produced by chemical synthesis together with a thioreductase motif, leading to sequence CPYC-LF-LKSDGRVKYTLN [SEQ ID NO:21]

Such sequence contains 1 arginine (R) at position P6. This R residue is replaced with citrulline, a amino acid obtained by the action of peptidyl arginine deiminase. This modification results in the loss of a positive charge leading to a higher interaction with MHC class II anchoring residues at P6.

The final sequence of the peptide used for vaccination is therefore CPYC-LF-LKSDG-citrulline-VKYTLN [SEQ ID NO:22].

Patients affected by Fabry disease are immunized with peptide of SEQ ID NO:21, using a standard procedure of peptide adsorbed on aluminium hydroxide and administered by SC injection. Epitope-specific cytolytic CD4+ T cells are then produced.

Such vaccinated patients can then be administered with recombinant alpha-galactosidase modified as to contain the LFLKSDGRVKYTLN sequence [SEQ ID NO: 20] of the promiscuous epitope [SEQ ID NO:23].

Example 4: Cell Therapy

Patients under immunosuppressive therapy could benefit from administration of a therapeutic antibody, yet active vaccination using peptides encompassing class II restricted epitopes could be difficult under such circumstances.

However, it is possible to collect cells from peripheral blood of such patients, prepare naïve CD4+ T cells for in vitro transformation into cytolytic cells, which can then be re-administered to the patient in a strictly autologous manner. By doing so, the patient is immediately protected towards unwanted immune responses to the therapeutic agent considered. One representative example of such situation is multiple sclerosis, with patients under immunosuppressive therapy, who could benefit from the administration of antibodies such as the anti-CD52 specific antibody (Campath-1H, Alemtuzumab).

A fifty ml sample of peripheral blood is collected from such patients and naïve CD4+ T cells are prepared by magnetic bead adsorption. Dendritic cells are derived from the monocytes obtained from the same blood sampling, using methods known in the art.

A promiscuous class II-restricted epitope of *mycobacterium* cell entry protein, Mce2, DPIELNATLSAVA [SEQ ID NO:24] (amino acids 163 to 175) was chosen (Panigada (2002) *Infect. Immun.* 70, 79-85).

A thioreductase motif was added at the amino-terminal end of this peptide to generate the sequence CPYC-DPIELNATLSAVA [SEQ ID NO:25]

Dendritic cells are loaded with peptide of SEQ ID NO:25 and naïve CD4+ T cells are stimulated four times for 7 days with these dendritic cells to generate cytolytic CD4+ T cells.

$5 \times 10^6$ cytolytic cells are administered by the IV route to the cell donor.

An anti-CD52 specific antibody was obtained by genetic engineering, which contain the sequence DPIELNATLSAVA [SEQ ID NO:24] added to the amino-terminal end of the molecule, with 2 glycine residues as a linker [SEQ ID NO:26].

Administration of such modified anti-CD52 antibody to an individual having received autologous CD4+ T cells activated in vitro with peptide of SEQ ID NO:25 results in activation of cytolytic CD4+ T cells to the peptide DPIELNATLSAVA [SEQ ID NO:24], thereby preventing any possibility to elicit an immune response towards the therapeutic antibody.

Example 5: Vector for Expression of Protein in Fusion with Modified CLIP Promiscuous Epitope The mammalian expression vector pCMV with cytomegalovirus promotor is engineered to allow the expression in CHO (Chinese hamster ovary) cells of any protein for replacement therapy, in fusion with the promiscuous CLIP-derived epitope described in example 2 [SEQ ID NO:17]. Patients in need for injection with a protein for replacement therapy are first vaccinated by administration of a peptide comprising a thioreductase motif and the modified CLIP-derived epitope described in example 2 [SEQ ID NO:18]. This immunization is known to elicit epitope-specific cytolytic CD4+ T cells, as described in patent application WO200817517.

The therapeutic protein of interest, in the form of a fusion protein, flanked by the CLIP sequence retains its full activity upon administration and activates the cytolytic CD4+ T cells obtained by vaccination, thereby precluding any detrimental immune response. The promiscuous nature of the CLIP-modified epitope makes it possible to use the same vaccine and the same EPO molecule for any patient in need of such therapy, regardless of its HLA profile.

To obtain this expression vector, an adaptor was engineered consisting of CLIP-derived epitope preceded by a linker made of 2 glycines and surrounded by restriction enzyme specific sequences Xho-I/Nhe-I as shown below:

```
                Xhol(*)
    GCA CGG CTC GAG GGC GGA AAG TTT TTC ATG GCC ACC
                     G   G   K   F   F   M   A   T
    CGT GCC GAG CTC CCG CCT TTC AAA AAG TAC CGG TGG
                    10              20              30

NheI(*)
    AGA CTG CTG ATG CAG GCG CTG AGC TAG CTA GTT C      SEQ ID NO: 38
     R   L   L   M   Q   A   L   S   *                 SEQ ID NO: 39
    TCT GAC GAC TAC GTC CGC GAC TCG ATC GAT CAA G
            40              50              60
```

By cloning the adaptor into the commercially available expression vector pCMV, modified expression pCMV-CLIP is created with a multiple cloning site for the insertion of Erythropoietin (EPO) cDNA. For this purpose, the sequence coding for EPO was amplified by PCR with a forward primer consisting of the EPO specific sequence and Age-I specific sequence preceded by a KOZAK sequence, and a reverse primer made of EPO specific sequence and Sal-I specific sequence. After digestion Age-I/Sal-I, the EPO construct is inserted into pCMV-CLIP, pre-digested by Age-I and Xho-I. The plasmid is transformed and amplified in DH5-alpha *E. coli*. After purification and linearization, the expression vector for EPO-CLIP fusion protein is transfected into CHO cells. Then transfected CHO cells were selected on ampicillin and the clone producing the higher level of EPO-CLIP was selected for mass production of the recombinant fusion protein with SEQ ID NO: 40 (modified CLIP sequence underlined)

[SEQ ID NO: 40]
MGVHECPAWL WLLLSLLSLP LGLPVLGAPP RLICDSRVLE

RYLLEAKEAE NITTGCAEHC SLNENITVPD TKVNFYAWKR

-continued

MEVGQQAVEV WQGLALLSEA VLRGQALLVN SSQPWEPLQL

HVDKAVSGLR SLTTLLRALR AQKEAISPPD AASAAPLRTI

-continued

TADTFRKLFR VYSNFLRGKL KLYTGEACRT GDRVEGG<u>KFF</u>

<u>MATRLLMQAL</u> S

Example 6: Sequences Disclosed in the Application

| SEQ ID NO: | Sequence |
|---|---|
| 1 | [FWYHT]-X(2)-[VILM]-X(2)-[FWYHT] |
| 2 | C-X(2)-C |
| 3 | C-X(2)-S |
| 4 | C-X(2)-T |
| 5 | S-X(2)-C |
| 6 | T-X(2)-C |
| 7 | [CST]-X(2)-C |
| 8 | C-X(2)-[CST] |
| 9 | KMRMATPLLMQAL |
| 10 | [VILMFWYH][RVILMFWYH]MAT[PR]LLM |
| 11 | aKXVAAWTLKAAaZC (a = D-Alanine, X = 1-cyclohexylalanine, Z = aminocaproic acid) |
| 12 | QGYK VLVLNPSVAA T |
| 13 | TTVRLRA YMNTPGLPV |
| 14 | CPYCVRVLVLNPSVAA |
| 15 | CPYCVRYMNTPGLPV |
| 16 | QGYKVLVLNP SVAATTTVRL RAYMNTPGLP VQVQLQQPGA ELVKPGASVK MSCKASGYTF TSYNMHWVKQ TPGRGLEWIG AIYPGNGDTS YNQKFKGKAT LTADKSSSTA YMQLSSLTSE DSAVYYCARS TYYGGDWYFN VWGAGTTVTV SAASTKGPSV FPLAPSSKST SGGTAALGCL VKDYFPEPVT VSWNSGALTS GVHTFPAVLQ SSGLYSLSSV VTVPSSSLGT QTYICNVNHK PSNTKVDKKV EPKSCDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |
| 17 | KFFMATRLLMQAL |
| 18 | CPYCVRFFMATRLLMQAL |
| 19 | APPRLICDSR VLERYLLEAK EAENITTGCA EHCSLNENIT VPDTKVNFYA WKRMEVGQQA VEVWQGLALL SEAVLRGQAL LVNSSQPWEP LQLHVDKAVS GLRSLTTLLR ALGAQKEAIS PPDAASAAPL RTITADTFRK LFRVYSNFLR GKLKLYTGEA CRTGDRGGKF FMATRLLMQA L |
| 20 | LFLKSDGRVKYTLN |
| 21 | CPYCLFLKSDGRVKYTLN |
| 22 | CPYCLFLKSDG-citrulline-VKYTLN |
| 23 | LFLKSDGRVK YTLNDNGLAR TPTMGWLHWE RFMCNLDCQE EPDSCISEKL FMEMAELMVS EGWKDAGYEY LCIDDCWMAP QRDSEGRLQA DPQRFPHGIR QLANYVHSKG LKLGIYADVG NKTCAGFPGS FGYYDIDAQT FADWGVDLLK FDGCYCDSLE NLADGYKHMS LALNRTGRSI VYSCEWPLYM WPFQKPNYTE IRQYCNHWRN FADIDDSWKS IKSILDWTSF NQERIVDVAG PGGWNDPDML VIGNFGLSWN QQVTQMALWA IMAAPLFMSN DLRHISPQAK ALLQDKDVIA INQDPLGKQG YQLRQGDNFE VWERPLSGLA WAVAMINRQE IGGPRSYTIA VASLGKGVAC NPACFITQLL PVKRKLGFYE WTSRLRSHIN PTGTVLLQLE NTMQMSLKDL L |
| 24 | DPIELNATLSAVA |
| 25 | CPYCDPIELNATLSAVA |

| SEQ ID NO: | Sequence |
|---|---|
| 26 | DPIELNATLS AVAGGQVQLQ ESGPGLVRPS QTLSLTCTVS GFTFTDFYMN WVRQPPGRGL EWIGFIRDKA KGYTTEYNPS VKGRVTMLVD TSKNQFSLRL SSVTAADTAV YYCAREGHTA APFDYWGQGS LVTVSSASTK GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKKVEPKSCD KTHTCPPCPA PELLGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSRDELTKN QVSLTCLVKG FYPSDIAVEW ESNGQPENNY KTTPPVLDSD GSFFLYSKLT VDKSRWQQGN VFSCSVMHEA LHNHYTQKSL SLSPGK |
| 27 | [FWYH]-X(2)-[VILM]-X(2)-[FWYH] |
| 28 | [FWY]-X(2)-[VILM]-X(2)-[FWY] |
| 29 | X1X2MATX6LLM [SEQ ID NO: 29], X1 and X2 are V, I, L, M, F, H, Y or W, X6 is R or P. |
| 30 | FFMATRLLM |
| 31 | WWMATRLLM |
| 32 | WFMATRLLM |
| 33 | FWMATRLLM |
| 34 | FFMATPLLM |
| 35 | WWMATPLLM |
| 35 | WFMATPLLM |
| 37 | FWMATPLLM |
| 38 | gca cgg ctc gag ggc gga aag ttt ttc atg gcc acc aga ctg ctg atg cag gcg ctg agc tag cta gtt c |
| 39 | GGKFFMATRLLMQALS |
| 40 | MGVHECPAWL WLLLSLLSLP LGLPVLGAPP RLICDSRVLE RYLLEAKEAE NITTGCAEHC SLNENITVPD TKVNFYAWKR MEVGQQAVEV WQGLALLSEA VLRGQALLVN SSQPWEPLQL HVDKAVSGLR SLTTLLRALR AQKEAISPPD AASAAPLRTI TADTFRKLFR VYSNFLRGKL KLYTGEACRT GDRVEGGKFF MATRLLMQAL S |

The invention claimed is:

1. A kit of parts of polypeptides comprising:
   a) a peptide comprising:
      a1) a first peptide sequence comprising an MHC class II T cell epitope, and
      a2) immediately adjacent to said first peptide sequence or separated by at most 7 amino acids from said first peptide sequence a [CST]-X(2)-C [SEQ ID NO:7] or C-X(2)-[CST] [SEQ ID NO:8] oxidoreductase motif sequence, and
   b) a fusion polypeptide comprising as fusion partners:
      b1) a therapeutic protein and
      b2) the first peptide sequence defined in a1), wherein the first peptide sequence does not occur in the sequence of the protein of b1).

2. The kit of parts according to claim 1, wherein the oxidoreductase motif sequence is C-X(2)-C [SEQ ID NO: 2].

3. The kit of parts according to claim 1, wherein said MHC class II T cell epitope is a promiscuous epitope binding to one or more HLA-DR1 molecules.

4. The kit of parts according to claim 1, wherein said MHC class II T cell epitope has the sequence $X_1X_2MATX_6LLM$ [SEQ ID NO: 29], wherein $X_1$ and $X_2$ are independently selected from V, I, L, M, Y, H, F and W, and $X_6$ is R or P.

5. A method of reducing the clearance of the fusion polypeptide of claim 1 b) caused by antigen presentation by antigen-presenting cells in an individual, comprising administering to said individual
   a) an effective amount of the peptide of claim 1 a); and
   b) the fusion polypeptide of claim 1 b) or a polynucleotide encoding the fusion polypeptide of claim 1 b).

6. The method according to claim 5, wherein step b) comprises administering the fusion polypeptide of claim 1 b).

7. A method for preparing a kit of parts of polypeptides according to claim 1, comprising:
   i) preparing the polypeptide of b),
   ii) preparing the peptide of a), and
   iii) placing the polypeptide of b) and peptide of a) in a kit.

8. A method comprising administering to a subject in need thereof an effective amount of
   a) the peptide of claim 1 a); and
   b) the fusion polypeptide of claim 1 b) or a polynucleotide encoding the fusion polypeptide of claim 1 b), wherein the therapeutic protein is an antibody, coagulation factor, fibrinolytic peptide, hormone, cytokine or growth factor.

9. The method according to claim 8, wherein step b) comprises administering the fusion polypeptide of claim 1 b).

10. The method according to claim 8, wherein the therapeutic protein is an antibody.

11. The method according to claim 8, wherein the therapeutic protein is a coagulation factor.

12. The method according to claim 8, wherein the therapeutic protein is a growth factor.

* * * * *

UNITED STATES PATENT AND TRADEMARK OFFICE
CERTIFICATE OF CORRECTION

PATENT NO. : 11,787,849 B2  
APPLICATION NO. : 15/761223  
DATED : October 17, 2023  
INVENTOR(S) : Jean-Marie Saint-Remy et al.

Page 1 of 1

It is certified that error appears in the above-identified patent and that said Letters Patent is hereby corrected as shown below:

In the Claims

Column 51, Line 38: Please change "b2) the first peptide sequence defined in al)" to --b2) the first peptide sequence defined in a1)--

Signed and Sealed this  
Fifth Day of December, 2023

Katherine Kelly Vidal  
*Director of the United States Patent and Trademark Office*